United States Patent
Myntti

(10) Patent No.: US 10,477,860 B2
(45) Date of Patent: *Nov. 19, 2019

(54) HIGH OSMOLARITY ANTIMICROBIAL COMPOSITION CONTAINING ONE OR MORE ORGANIC SOLVENTS

(71) Applicant: Next Science IP Holdings Pty Ltd, Chatswood, NSW (AU)

(72) Inventor: Matthew Franco Myntti, St. Augustine, FL (US)

(73) Assignee: Next Science IP Holdings Pty Ltd, Chatswood, NSW (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/976,806

(22) Filed: May 10, 2018

(65) Prior Publication Data

US 2018/0255767 A1    Sep. 13, 2018

Related U.S. Application Data

(63) Continuation of application No. 14/888,437, filed as application No. PCT/US2014/036677 on May 2, 2014, now Pat. No. 10,021,876.

(Continued)

(51) Int. Cl.
| | |
|---|---|
| *A01N 25/02* | (2006.01) |
| *A01N 33/12* | (2006.01) |
| *A61K 8/33* | (2006.01) |
| *A61K 8/34* | (2006.01) |
| *A61K 8/39* | (2006.01) |
| *A61K 8/41* | (2006.01) |
| *A61K 8/46* | (2006.01) |
| *A61Q 17/00* | (2006.01) |

(Continued)

(52) U.S. Cl.
CPC ............ *A01N 25/02* (2013.01); *A01N 31/02* (2013.01); *A01N 33/12* (2013.01); *A01N 37/02* (2013.01); *A01N 37/40* (2013.01); *A01N 41/10* (2013.01); *A61K 8/33* (2013.01); *A61K 8/34* (2013.01); *A61K 8/39* (2013.01); *A61K 8/416* (2013.01); *A61K 8/463* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 2009/0148502 A1* | 6/2009 | Pronovost | A61L 15/18 514/1.1 |
| 2010/0086576 A1* | 4/2010 | Myntti | A01N 25/30 424/405 |

OTHER PUBLICATIONS

Examination report dated Jan. 1, 2018 in India patent appl. No. 10847/DELNP/2015—7 pp.

(Continued)

*Primary Examiner* — Carlos A Azpuru
*Assistant Examiner* — Casey S Hagopian
(74) *Attorney, Agent, or Firm* — Zollinger & Burleson Ltd.

(57) ABSTRACT

A composition that can solvate biofilms and disrupt bacterial cell walls acts to both kill the bacteria by cell lysis and remove the biofilm. This solvent-containing composition is effective against a broad spectrum of microbes and can be used on a variety of surfaces, both living and inanimate. The polarity of the solvent component of the composition is lower than that of pure water so that the composition exhibits increased efficacy in solvating the macromolecular matrix of a biofilm and in penetrating bacterial cell walls.

20 Claims, 9 Drawing Sheets

Related U.S. Application Data

(60) Provisional application No. 61/818,586, filed on May 2, 2013, provisional application No. 61/873,500, filed on Sep. 4, 2013.

(51) Int. Cl.
*A01N 37/02* (2006.01)
*A01N 37/40* (2006.01)
*A01N 31/02* (2006.01)
*A01N 41/10* (2006.01)

(56) References Cited

OTHER PUBLICATIONS

Examination report dated Jul. 15, 2019 in EP patent appl. No. 14 791 925.2.

* cited by examiner

HIGH OSMOLARITY ANTIMICROBIAL COMPOSITION CONTAINING ONE OR MORE ORGANIC SOLVENTS

CROSS-REFERENCE TO RELATED APPLICATIONS

This application is a continuation of U.S. patent application Ser. No. 14/888,437, having a 371(c) date of 1 Nov. 2015 and now issued as U.S. Pat. No. 10,021,876, which is a national stage entry application of international application PCT/US2014/036677, filed 2 May 2014, which claims priority to and the benefit of U.S. patent appl. Nos. 61/818,586, filed 2 May 2013, and 61/873,500, filed 4 Sep. 2013, the disclosures of all of which are incorporated herein by reference in their entireties.

BACKGROUND INFORMATION

Bacteria are responsible for a significant amount of disease and infection. Ridding surfaces of bacteria is desirable to reduce human exposure. Because bacteria have developed self-preservation mechanisms, they are extremely difficult to remove and/or eradicate.

Bacteria can be found in several forms, including planktonic and biofilm. In a biofilm, bacteria interact with surfaces and form colonies which adhere to a surface and continue to grow. The bacteria produce exopolysaccharide (EPS) and/or extracellular-polysaccharide (ECPS) macromolecules which crosslink to form matrices or films that help to keep the bacteria attached to the surface In addition to adhering to surfaces, biofilm matrices protect bacteria against many forms of attack. Protection likely involves both the small diameter of the flow channels in the matrix, which restricts the size of molecules that can transport to the underlying bacteria, and consumption of biocides through interactions with constituent EPS and/or ECPS macromolecules.

Additionally, bacteria in biofilm form are down-regulated (sessile) and not actively dividing. This makes them resistant to attack by a large group of antibiotics and antimicrobials, many of which attack the bacteria during the active parts of their lifecycle, e.g., cell division.

Due to protection afforded by the macromolecular matrix and their down-regulated state, bacteria in a biofilm are very difficult to treat. The types of biocides and antimicrobials that can effectively treat bacteria in this form are strongly acidic or oxidizing, often involving halogen atoms, oxygen atoms, or both. Common examples include concentrated bleach, strong mineral acids (e.g., HCl), high concentrations of quaternary ammonia compounds and aldehydes, and $H_2O_2$. Commonly, large dosages of such chemicals are allowed to contact the biofilm for extended amounts of time (up to 24 hours in some circumstances), which makes them impractical for many applications.

Formulations that disrupt the macromolecular matrices or bypass and/or disable the defenses inherent in these matrices have been described in U.S. Pat. Publ. Nos. 2010/0086576 and 2012/0059263. These formulations are aqueous compositions containing an acid or base, a buffering salt added at sufficient concentration to yield a relatively high osmolarity, and large amounts of surfactant, with the solutes creating an osmotic pressure differential across the bacteria cell wall and the surfactant(s) weakening those walls by interacting with wall proteins.

The foregoing compositions usually do not immediately break down the biofilm macromolecular matrix and, instead, transform that matrix into a gel-like state, which still provides some shielding of the bacteria. The aggregate efficacy and disinfection rate of these compositions thus are limited by the flux rate of the active ingredient(s) moving through the biofilm matrix and rate of bacterial cell wall degradation. (Disruption of the EPS decreases the mean free path that the antimicrobial components must travel.)

Further, regulatory bodies such as the U.S. Food and Drug Administration and Environmental Protection Agency have set threshold amounts for surfactants such as benzalkonium chloride and cetylpyridinium chloride. Any composition that includes such surfactants in amounts above those thresholds must be reviewed for safety prior to commercial introduction for certain applications such as, but not limited to, food contact (without rinsing), oral rinses, medical instrument sterilization, and skin contact. The foregoing compositions have surfactant concentrations that usually exceed regulatory threshold amounts.

SUMMARY

Provided herein is an antimicrobial composition that is effective against bacteria in a variety of states, even when the composition is at or near neutral pH values. In addition to being lethal toward a wide spectrum of gram positive and gram negative bacteria, the composition also exhibits lethality toward other microbes such as viruses, fungi, molds, yeasts, and bacterial spores. In many embodiments, the composition has little or no toxicity to humans and animals.

The antimicrobial composition includes a solvent component and a solute component that is present in an amount sufficient to result in an overall osmolarity of the composition of at least 500, typically at least 575, and commonly at least 650 mOsm/L. The solvent component includes one or more organic liquid(s) which are chosen so that the solvent component exhibits a $\delta_p$ value below ~15.1, where $\delta_p$ is the dipolar intermolecular force (polarity) Hansen Solubility Parameter (HSP).

The high osmolarity of the composition combined with the correct solvent parameter(s), even in the absence of a surfactant, can quickly solvate a biofilm's macromolecular matrix and bacterial cell wall proteins. Solvent component (s) exhibiting the required $\delta_p$ value have been found to better, more efficiently solubilize microbe cell wall proteins. By bringing some portion of these cell wall proteins into solution, the entrained bacteria more easily can be caused to undergo cell leakage which, combined with the high partial pressure across their cell walls leads to bacterial death. Additionally, enhancing macromolecular matrix dissolution and increasing its solubility in the solvent system permits a shorter mean free path for the active components (the chemicals which interact with the bacteria), thereby increasing their rate and density and decreasing their necessary contact time and/or severity. These advantages permit use of compositions with lower total ingredient concentrations and/or milder conditions (e.g., pH) to be used.

While near neutral pH compositions are effective, the pH of the composition typically is moderately low (about 4≤pH≤6) or moderately high (about 8≤pH≤10). Higher and lower pH values may increase efficacy by permitting the composition to more efficiently disrupt the macromolecular matrix of a biofilm, perhaps by reacting or complexing with crosslinking metal ions.

At least some of the osmotically active solutes may include the dissociation product(s) of one or more acids or bases that are effective at interrupting or breaking ionic crosslinks in the macromolecular matrix of the biofilm, which facilitates passage of the solutes, and surfactant if used, through the matrix to the bacteria entrained therein and/or protected thereby.

Also provided are methods of using the foregoing composition. In an exemplary method, a composition of the type described above can be applied to a biofilm so as to effect at least a 3 log reduction in the number of live bacteria. For example, application of an inventive composition to a biofilm tested in accordance with the Center for Disease Control (CDC) biofilm reactor test method described below can provide at least a 3 log reduction in the number of live bacteria after a residence time of 5 minutes.

Also provided are methods of making the composition. In an exemplary method, a target $\delta_p$ is identified, one or more solvents having a $\delta_p$ within 0.5 MPa$^{1/2}$ of the target is/are identified, and the solvent(s) is/are blended with sufficient solutes to provide a composition having an osmolarity of at least 500, 600, 700, or 800 mOsm/L.

In another exemplary method, an aqueous composition that includes one or more solutes can be modified by addition of one or more organic liquids so as to provide the composition with a target $\delta_p$ that is less than the $\delta_p$ of the original (aqueous) composition.

The composition can be incorporated into a semi-viscous gel or adherent coating from which the active components can elute over time or remain entrained within the gel or coating to prevent colonization of the gel or coated surface. In the case of a gel, the composition can employ any of a variety of water-miscible ointment bases, with choice providing control over elution rate from the gel to provide continuous application of the antimicrobial composition, to dissolve in place so as to provide a burst dose of product, or to elute to cover the surface.

At times, a single bacterial strain may be of particular interest or concern. In those cases, a composition that is particularly effective against that bacteria can be formulated due to differences in cell wall proteins of the different bacterial species. This can be quite beneficial in situations where eliminating a pathogenic bacteria while not affecting the remainder of the microflora is desired. (In these cases, the composition likely will employ a different target $\delta_p$ than that described above, which is intended for broad spectrum efficacy; using a polarity at or near that target would be expected to kill all of the microbes exposed to the composition.)

The enhanced effectiveness of the composition permits lower concentrations of surfactant to be used. Although not absolutely required, the presence of a surfactant, particularly a polar surfactant, increases the efficacy of these formulations and increases the rate at which the composition acts against the targeted microbe(s). This is most likely due to the surfactant inducing cell lysis by attaching to those portions of the cell wall proteins that are solubilized by the solvent component.

The relevant portion(s) of any specifically referenced patent and/or published patent application is/are incorporated herein by reference.

DETAILED DESCRIPTION

Figure 1A:
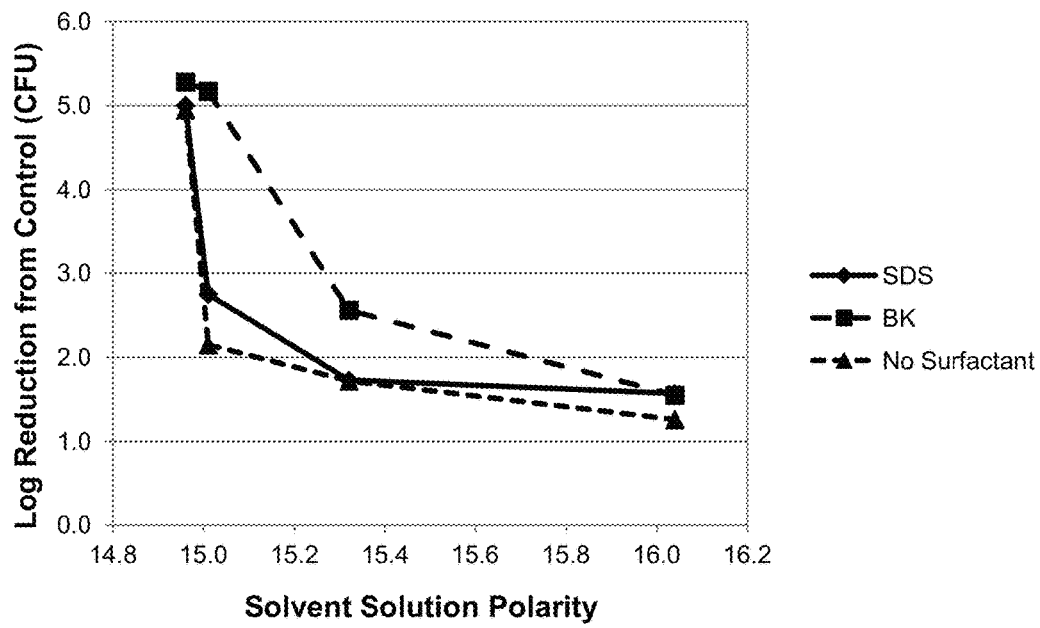
FIGS. 1a and 1b depict quantitative carrier testing results for compositions at pH=4 and pH=10, respectively, employing anionic surfactant, cationic surfactant, and no surfactant, with S. aureus bacterial reductions plotted against $\delta_p$ values of the solvent component of antimicrobial compositions.

The foregoing summary explanation made mention of HSP, a common method for predicting whether one material will dissolve in another to form a solution, and the HSP values for most commonly used solvents are well documented. (A number of alternative methods to determine the solubility of solutes within a solvent are available. The most common alternative is the Hildebrand solubility parameter, which measures the cohesive energy densities of the solvent and solute and compares them for similarity. The polar forces are not separated from the dispersive and hydrogen bonding forces and, for reasons that become apparent below, this makes the Hildebrand solubility parameter somewhat less desirable as a measurement/choice tool. Nevertheless, the ordinarily skilled artisan will recognize that it, as well as other methods, can be used to identify appropriate organic liquids and/or solvent combinations.)

Each component in a mixture or composition has three HSPs: dispersion, dipole-dipole (polarity) interactions, and hydrogen bonding. These parameters are generally treated as coordinates in three dimensions, with HSP characterizations being visualized using a spherical representation: the 3D coordinates are at the center of the sphere with the radius of the sphere ($R_0$ or "interaction radius") indicating the maximum difference in affinity tolerable for a "good" interaction with a solvent or solute. In other words, acceptable solvents lie within the interaction radius, while unacceptable ones lie outside it.

The distance between the HSPs of two materials in so-called Hansen space ($R_a$) can be calculated according to the following formula:

$$(R_a)^2 = 4(\delta_{d2} - \delta_{d1})^2 + (\delta_{p2} - \delta_{p1})^2 + (\delta_{h2} - \delta_{h1})^2 \quad (I)$$

where $\delta_d$ is the energy from dispersion forces between the molecules, $\delta_p$ is the energy from dipole-dipole intermolecular forces, and $\delta_h$ is the energy from hydrogen bonds between molecules.

A simple composite affinity parameter, the Relative Energy Difference (RED), represents the ratio of the calculated HSP difference ($R_a$) to the interaction radius ($R_0$), i.e., RED=$R_a/R_0$. In situations where RED<1.0, the solubilities of the molecules are sufficiently similar that one will dissolve in the other. In situations where RED>1.0, the solubilities of the molecules are not sufficiently similar for one to dissolve the other. In situations where RED≈1.0, partial dissolution is possible.

Regression analysis of data collected during development of the present composition has shown that each of the $\delta_p$, $\delta_d$, and $R_a$ values correlates with composition effectiveness. (Because of the direct correlation within this data between the $\delta_p$, $\delta_d$, and $R_a$ values, compositions that have solvent components that have the stated $\delta_p$ values also can be described in terms of $\delta_d$ and $R_a$ values.)

Two regression analysis statistics of interest are the F- and p-values. The F-value is calculated by dividing the test factor (e.g., $\delta_p$) mean square by the test error (non-assigned variation) mean square, with higher numbers meaning that the test factor is more important than random chance. (Mean square is the sum of squares divided by the degrees of freedom.) The p-value is the probability of obtaining a test statistic that is at least as extreme as the calculated value if the null hypothesis is true (in this case, probability that the increase in efficacy is due to random chance and that there is no difference between adding and not adding solvent).

Despite $\delta_p$, $\delta_d$, and $R_a$ values all correlating with composition effectiveness, the F and p-values based on only the $\delta_p$ value have the highest correlation. Possible reasons for the dominant importance of the $\delta_p$ factor include the protein molecules on the surface of the bacteria being crosslinked in place and the relative unimportance for the entire protein to be solubilized for efficacy, i.e., only a portion of the protein must be solubilized to allow the solute, optionally with acid/base and/or surfactant, to induce leakage of cell contents through or across the membrane.

The dipole-dipole interaction Hansen solubility parameter for a particular solution or mixture of solvents can be calculated according to the following formula:

$$\delta_p = \sum_{i=1}^{n} (\delta_{di} \times x_{di}) \quad \text{(II)}$$

where $\delta_h$ is the energy from dipolar intermolecular force for solvent i, $x_{di}$ is the percentage of solvent i in the solvent portion of the composition, and n is the total number of solvent components.

Hereinthroughout, the $\delta_p$ value for a given solvent or combination of solvents is determined at room temperature (because solubility typically increases with increasing temperature, meaning that the dissolution rate of the macromolecular matrix and the bacterial cell wall proteins will increase, the efficacy of the inventive composition is expected to increase at higher temperatures) and pH values are those which can be obtained from any of a variety of potentiometric techniques employing a properly calibrated electrode.

Turning now to the composition, it can contain as few as two components: a solvent having a $\delta_p$ value low enough to permit some of the bacterial cell wall proteins to become solubilized and a solute capable of raising the osmolarity of the system to a level high enough to induce cell lysis. As discussed below, the efficacy of the composition often can be positively impacted by including sufficient acid or base to move the pH away from neutral and/or one or more types of surfactant.

While ingredients used to prepare or provide such components typically are ineffective against bacteria in biofilm form when used at concentrations commonly employed in commercial products, an appropriately formulated composition can be very effective at breaking down or bypassing and disabling biofilm defenses, thereby allowing the composition to solvate some portion of the bacterial cell wall proteins and induce bacterial membrane leakage, leading to cell lysis, thereby killing even bacteria in a sessile state.

The solvent component typically includes water ($\delta_p$≈16.0 $MPa^{1/2}$) and at least one organic liquid with a $\delta_p$ value lower than that of water.

Water commonly is employed in the solvent component of the composition due to its high solute holding capability (which allows for higher osmolarity compositions), wetting properties, excellent biocompatibility, environmental friendliness, and low cost. Essentially any source of water can be used, although those that are relatively free of bacteria without advance treatment are preferred. The water need not be distilled, deionized, or the like, although such treatments certainly are not excluded. To enhance solubility of one or more of the other components of the composition, the water can be heated.

Where the solvent component contains water and one or more organic liquids, the latter acts to reduce the $\delta_p$ value of the solvent component to a point where the solvent system better solubilizes one or more of the proteins of the bacterial cell walls. In other words, the $R_a$ of the solvent system is such that it is less than or equal to the $R_0$ of at least one bacterial cell wall protein, i.e., the solvent system-protein RED is no more than ~1.0.

The $\delta_p$ value of the overall solvent component is less than 16.0, generally less than ~15.8, less than ~15.6, less than ~15.4, or less than ~15.2, preferably no more than ~15.1, no more than ~15.0, no more than ~14.8, no more than ~14.6, no more than ~14.4, no more than ~14.2, or no more than ~14.0 MPa$^{1/2}$. For broad spectrum effectiveness, the $\delta_p$ value of the overall solvent component generally ranges from 13.1 to 15.7 MPa$^{1/2}$, commonly from 13.3 to 15.6 MPa$^{1/2}$, typically from 13.5 to 15.5 MPa$^{1/2}$, and most typically from 13.7 to 15.4 MPa$^{1/2}$.

With respect to the organic liquid(s), practically any having a $\delta_p$ value less than ~2, less than ~3, less than ~4, less than ~5, less than ~6, less than ~7, less than ~8, less than ~9, less than ~10, less than ~11, less than ~12, less than ~13, less than ~14, less than ~14.2, less than ~14.4, less than ~14.6, less than ~14.8, less than ~15.0, less than ~15.1, less than ~15.2, less than ~15.3, or less then ~15.5 MPa$^{1/2}$ can be used. Non-limiting examples of organic liquids having such $\delta_p$ values are provided in Tables 1 and 2 below.

When used in conjunction with water, such a material(s) commonly is present at concentrations of from 0.1 to ~33%, 0.25 to ~25%, 0.5 to ~20%, ~1 to ~15%, ~2 to ~12%, ~3 to ~11%, ~4 to ~10%, or ~5 to ~10%, with all of the foregoing representing w/v measurements, i.e., grams of organic liquid(s) per liter of total solvent component of the composition.

The amount of a given organic liquid (or mixture of organic liquids) to be added to water can be calculated using formula (II) if a targeted $\delta_p$ value is known. Similarly, a projected $\delta_p$ value can be calculated using formula (II) if the amount of organic liquid(s) and their individual $\delta_p$ values are known. Methods of formulating antimicrobial compositions based on both such techniques are contemplated.

Although the presence of water in the solvent component is preferred for reasons explained above, an organic liquid or a mixture of multiple organic liquids, each having a $\delta_p$ value less than 15.5 MPa$^{1/2}$ or the solution thereof having an overall $\delta_p$ value less than 15.5 MPa$^{1/2}$, that can solvate the solute component (and other optional ingredients) without the presence or addition of water can be used.

The solvent component can consist of, or consist essentially of, just organic liquids. In other embodiments, the solvent component can consist of, or consist essentially of, water and an organic liquid having $\delta_p$ value less than 15.5 MPa$^{1/2}$. In yet other embodiments, the solvent component can consist of, or consist essentially of, water and two or more organic liquids with the resulting solvent component having $\delta_p$ value less than 15.5 MPa$^{1/2}$.

With respect to organic liquids, preferred compounds include ethers and alcohols due to their low tissue toxicity and environmental friendliness. These can be added at concentrations up to the solubility limit of the other ingredients in the composition.

Ether-based liquids that can be used in the solvent component include those defined by the following general formula $$R^1(CH_2)_xO-R^2-[O(CH_2)_z]_yZ \qquad (III)$$

where x is an integer of from 0 to 20 (optionally including, where 2≤x≤20, one or more points of ethylenic unsaturation), y is 0 or 1, z is an integer of from 1 to 4, $R^2$ is a $C_1$-$C_6$ linear or branched alkylene group, $R^1$ is a methyl, isopropyl or phenyl group, and Z is a hydroxyl or methoxy group. Non-limiting examples of glycol ethers (formula (III) compounds with Z=OH) that can be used in the solvent component are set forth below in Table 1.

TABLE 1

Representative glycol ethers, with formula (III) variables and $\delta_p$ values

|  | $R^1$ | x | $R^2$ | y | z | ~$\delta_p$ (MPa$^{1/2}$) |
|---|---|---|---|---|---|---|
| ethylene glycol monomethyl ether | $CH_3$ | 0 | $(CH_2)_2$ | 0 | — | 9.2 |
| ethylene glycol monoethyl ether | $CH_3$ | 1 | $(CH_2)_2$ | 0 | — | 9.2 |
| ethylene glycol monopropyl ether | $CH_3$ | 2 | $(CH_2)_2$ | 0 | — | 8.2 |
| ethylene glycol monoisopropyl ether | $(CH_3)_2CH$ | 0 | $(CH_2)_2$ | 0 | — | 8.2 |
| ethylene glycol monobutyl ether | $CH_3$ | 3 | $(CH_2)_2$ | 0 | — | 5.1 |
| ethylene glycol monophenyl ether | $C_6H_5$ | 0 | $(CH_2)_2$ | 0 | — | 5.7 |
| ethylene glycol monobenzyl ether | $C_6H_5$ | 1 | $(CH_2)_2$ | 0 | — | 5.9 |
| diethylene glycol monomethyl ether | $CH_3$ | 0 | $(CH_2)_2$ | 1 | 2 | 7.8 |
| diethylene glycol monoethyl ether (DGME) | $CH_3$ | 1 | $(CH_2)_2$ | 1 | 2 | 9.2 |
| diethylene glycol mono-n-butyl ether | $CH_3$ | 3 | $(CH_2)_2$ | 1 | 2 | 7.0 |
| propylene glycol monobutyl ether | $CH_3$ | 3 | $(CH_2)_3$ | 0 | — | 4.5 |
| propylene glycol monoethyl ether | $CH_3$ | 1 | $(CH_2)_3$ | 0 | — | 6.5 |
| propylene glycol monoisobutyl ether | $(CH_3)_2CH$ | 1 | $(CH_2)_3$ | 0 | — | 4.7 |
| propylene glycol monoisopropyl ether | $(CH_3)_2CH$ | 0 | $(CH_2)_3$ | 0 | — | 6.1 |
| propylene glycol monomethyl ether | $CH_3$ | 0 | $CH_2CH(CH_3)$ | 0 | — | 6.3 |
| propylene glycol monophenyl ether | $C_6H_5$ | 0 | $CH_2CH(CH_3)$ | 0 | — | 5.3 |
| propylene glycol monopropyl ether (PGME) | $CH_3$ | 2 | $CH_2CH(CH_3)$ | 0 | — | 5.6 |
| triethylene glycol monomethyl ether | $CH_3$ | 0 | $(CH_2)_2$ | 2 | 2 | 7.6 |
| triethylene glycol monooleyl ether | $CH_3$ | 17* | $(CH_2)_2$ | 2 | 2 | 3.1 |

*includes unsaturation at the 9 position

Alcohols that can be used include cyclic and $C_1$-$C_{16}$ acyclic (both linear and branched, both saturated and unsaturated) alcohols, optionally including one or more points of ethylenic unsaturation and/or one or more heteroatoms other than the alcohol oxygen such as a halogen atom, an amine nitrogen, and the like. Non-limiting examples of representative examples are compiled in the following table.

TABLE 2

Representative alcohols, with $\delta_p$ values

|  | ~$\delta_p$ (MPa$^{1/2}$) |
|---|---|
| 2-propenol | 10.8 |
| 1-butanol | 5.7 |
| t-butyl alcohol | 5.1 |
| 4-chlorobenzyl alcohol | 7.5 |
| cyclohexanol | 4.1 |

TABLE 2-continued

Representative alcohols, with $\delta_p$ values

| | $\sim\delta_p$ (MPa$^{1/2}$) |
|---|---|
| 2-cyclopentenyl alcohol | 7.6 |
| 1-decanol | 10.0 |
| 2-decanol | 10.0 |
| 2,3-dichloropropanol | 9.2 |
| 2-ethyl-1-butanol | 4.3 |
| ethanol | 8.8 |
| 2-ethyl-hexanol | 3.3 |
| isooctyl alcohol | 7.3 |
| octanol | 3.3 |
| methanol | 12.3 |
| oleyl alcohol | 2.6 |
| 1-pentanol | 4.5 |
| 2-pentanol | 6.4 |
| 1-propanol | 6.8 |
| 2-propanol (IPA) | 6.1 |

Other organic liquids may be used to achieve efficacy with good miscibility with water, examples of which include, but are not limited to, ketones such as acetone, methyl butyl ketone, methyl ethyl ketone and chloroacetone; acetates such as amyl acetate, ethyl acetate and methyl acetate; (meth)acrylates and derivatives such as acrylamide, lauryl methacrylate and acrylonitrile; aryl compounds such as benzene, chlorobenzene, fluorobenzene, toluene, xylene, aniline and phenol; aliphatic alkanes such as pentane, isopentane, hexane, heptane and decane; halogenated alkanes such as chloroform, methylene dichloride, chloroethane and tetrachloroethylene; cyclic alkanes such as cyclopentane and cyclohexane; and polyols such as ethylene glycol, diethylene glycol, propylene glycol, hexylene glycol, and glycerol. When selecting such organic liquids for use in the solvent component of the composition, possible considerations include avoiding those which contain a functional group that will react with either the acid(s)/base(s) or salt(s) employed in the composition and favoring those which possess higher regulatory pre-approval limits.

Tailoring the solvent concentrations and polarity value might permit targeting of a particular species or sub-genus of bacteria, for example, where a pathogenic bacteria on a tissue surface is suppressing native, beneficial flora (e.g., acne treatment). If the targeted bacteria has a known (or determinable) $\delta_p$ value that is outside the broad-spectrum efficacy region (e.g., it has $\delta_p$ value of 15.4 while the beneficial flora are stable at and somewhat below that $\delta_p$ value), a tailored composition with a solvent component having a $\delta_p$ value of 15.4 can be used to eradicate (wholly or substantially) the targeted bacteria while not killing the beneficial flora to flourish, thereby providing further benefits to the treated tissue after the pathogenic bacteria is removed.

Turning now to the solute component of the antimicrobial composition, the present compositions have high osmolarities, with efficacy generally increasing as osmolarity increases. However, in some applications where a reduced osmolarity is necessary or desirable, efficacy can be maintained at lower osmolarities as long as a threshold value necessary to induce an osmotic pressure imbalance across the bacterial cell wall is maintained. The presence of more of these solutes helps to negate the defense mechanisms provided by the EPS macromolecules of the matrix; in other words, having an abundance of solutes ensures that, even though many have been consumed by interaction with the macromolecular matrix, a sufficient amount arrive at the entrained bacteria to induce a high osmotic pressure across the bacterial cell wall membranes, leading to lysis.

This efficacy is independent of the particular identity or nature of individual compounds of the solute component, although smaller molecules are generally more effective than larger molecules due to solvent capacity (i.e., the ability to (typically) include more small molecules in a given amount of solvent component than an equimolar amount of larger molecules), relative ease of transport through the macromolecular matrix of a biofilm, and ease of transport across cell wall membranes. Charged, chelating molecules increase dissolution of the macromolecular matrix by removing the crosslinking metal ions between EPS chains, and accordingly are a preferred class of solutes.

Any of a number of solutes can be used to increase the composition osmolarity, which increases the differential osmotic pressure across the bacterial cell wall membrane.

One approach to achieve increased osmolarity of the composition is by adding large amounts of ionic compounds (salts); see, e.g., U.S. Pat. No. 7,090,882.

Where one or more organic acids or bases are used in the composition, a preferred, but not required, approach to increasing osmolarity involves inclusion of salt(s) of one or more the acid(s) or base(s) or the salt(s) of one or more other organic acids. For example, where the composition includes an acid, a many fold excess (e.g. 3× to 10× preferably, at least 5× or even at least 8×) of one or more salts of that acid also can be included. The identity of the countercation portion of the salt is not believed to be particularly critical, with common examples including ammonium ions and alkali metals. Where a polyacid is used, all or fewer than all of the H atoms of the carboxyl groups can be replaced with cationic atoms or groups, which can be the same or different. For example, mono-, di- and trisodium citrate all constitute potentially useful buffer precursors. However, because trisodium citrate has three available basic sites, it has a theoretical buffering capacity up to 50% greater than that of disodium citrate (which has two such sites) and up to 200% greater than that of sodium citrate (which has only one such site).

Regardless of how achieved, the osmolarity of the composition is at least moderately high, with an osmolarity of at least ~0.5 Osm/L being preferred for most applications. Depending on particular end-use application, the composition can have any of the following concentrations: at least ~0.6, at least ~0.75, at least ~1.0, at least ~1.5, at least ~1.75, at least ~2.0, at least ~2.25, at least ~2.5, at least ~2.75, at least ~3.0, at least ~3.25, and even at least ~3.5 Osm/L (with the upper limit being defined by the solubility limit of the solutes in the solvent component). Some applications, particularly those involving contact with human or animal tissue, usually involve relatively lower solute concentrations (e.g., 0.7 to 2.5 Osm/L, 0.8 to 2.45 Osm/L, 0.9 to 2.4 Osm/L, 0.95 to 2.35 Osm/L, and 1 to 2.33 Osm/L), while other applications, such as those requiring sterilization of inanimate objects, can employ relatively higher solute concentrations (e.g., 1 to 3.6 Osm/L, 1.1 to 3.5 Osm/L, 1.2 to 3.4 Osm/L, 1.3 to 3.3 Osm/L, 1.4 to 3.2 Osm/L, and 1.5 to 3.1 Osm/L). (As points of comparison, in biological applications, a 0.9% (by wt.) saline solution, which is ~0.3 Osm/L, typically is considered to be have moderate tonicity, while a 3% (by wt.) saline solution, which is ~0.9 Osm/L, generally is considered to be hypertonic.) Without wishing to be bound by theory, compositions having higher osmolarities may exert higher osmotic pressure on bacterial cell walls, which increases susceptibility to interruption by solvent and/or surfactant.

The solvent component increases the efficiency of the composition with respect to both macromolecular matrix dissolution and inducement of cell lysis. Accordingly, lower osmolarity compositions can be created which provide greater efficacy than counterpart compositions that do not contain the type of solvent component described above. In view of this enhanced efficiency, the values in the preceding paragraph can be reduced by 1%, 2%, 3%, 4%, 5%, 6%, 7%, 8%, 9%, 10%, 12%, 14%, 16%, 18% or even as much as ~20%.

With respect to pH, neutral embodiments of the present compositions can be efficacious. These neutral pH compositions might have reduced efficacy against some bacteria (albeit still superior to alternative technologies) compared to low or high pH counterparts but, conversely, are expected to be more effective than acidic or caustic counterparts for other species.

In general, moving the pH of a composition away from neutral results in increased efficacy due to an increase in the driving force for chelation of the metal ions crosslinking the EPS polymers, thereby increasing the rate at which the composition breaks down (or at least softens) the macromolecular matrix, and increases the efficacy of bacterial cell wall disruption and attack, thereby increasing the rate of cell lysis. This enhancement may not be linear, i.e., the enhancement in efficacy may be asymptotic past certain hydronium ion or hydroxide ion concentrations.

Compositions with very high and very low pH values, i.e., pH greater than ~10 or less than ~4, respectively, are not as environmental friendly or safe, but can be highly effective in some applications. For some applications where efficacy is more important than biocompatibility, the pH of the composition can be as low as ~2.0 or as high as ~12.5.

In vivo applications (including sinus rinses) commonly involve compositions with 4≤pH≤7. Dermal applications commonly employ compositions with 4≤pH≤9.5. As long as the pH of the composition is greater than ~3 or less than ~10, the composition generally will be biocompatible; specifically, external exposure will result in no long-term negative dermal effects and ingestion can result biodegradation and/or biosorption, particularly if diluted with water soon after ingestion. If the pH is greater than ~4 or less than ~10, accidental inhalation or exposure to an aerosolized version of the composition should not result in laryngospasms or other throat-related damage. However, even those embodiments of the composition having a pH below ~4 or greater than ~10 are believed to be significantly less toxic than presently available commercial products.

Hard surface cleaning, such as hospital and food service area disinfection, applications typically employ compositions with 4≤pH≤6 or 8≤pH≤10. More severe applications, such as sterilization of medical instruments and equipment, commonly involve compositions with 2≤pH≤4 or 9≤pH≤12.

From the foregoing, one can see that a composition having a pH other than neutral can be preferred. Preferred compositions include those with a pH value at least 0.5 units away from neutral, those with a pH value at least 1.0 unit away from neutral, those with a pH value at least 1.5 units away from neutral, those with a pH value at least 2.0 units away from neutral, those with a pH value at least 2.5 units away from neutral, those with a pH value at least 3.0 units away from neutral, those with a pH value at least 3.5 units away from neutral, those with a pH value at least 4.0 units away from neutral, and those with a pH value at least 4.5 units away from neutral.

Acidic forms of the present composition generally have a pH less than 6.8, less than 6.6, less than 6.4, less than 6.2, less than 6.0, less than 5.8, less than 5.6, less than 5.4, less than 5.2, less than 5.0, less than 4.8, less than 4.6, less than 4.4, less than 4.2, less than 4.0, less than 3.8, less than 3.6, less than 3.4, less than 3.2, less than 3.0, less than 2.8, less than 2.6, less than 2.4, less than 2.2, or even ~2.0. In terms of ranges, the pH can be from ~2 to ~6.7, from ~2.5 to ~6.5, from ~2.7 to ~6.3, from ~3 to ~6, from ~3.3 to ~5.7, or from ~3.5 to ~5.5.

Acidity can be achieved by adding to the solvent component (or vice versa) one or more acids. Strong (mineral) acids such as HCl, $H_2SO_4$, $H_3PO_4$, $HNO_3$, $H_3BO_3$, and the like or, preferably, organic acids, particularly organic polyacids may be used. Examples of organic acids include monoprotic acids such as formic acid, acetic acid and substituted variants (e.g., hydroxyacetic acid, chloroacetic acid, dichloroacetic acid, phenylacetic acid, and the like), propanoic acid and substituted variants (e.g., lactic acid, pyruvic acid, and the like), any of a variety of benzoic acids (e.g., mandelic acid, chloromandelic acid, salicylic acid, and the like), glucuronic acid, and the like; diprotic acids such as oxalic acid and substituted variants (e.g., oxamic acid), butanedioic acid and substituted variants (e.g., malic acid, aspartic acid, tartaric acid, citramalic acid, and the like), pentanedioic acid and substituted variants (e.g., glutamic acid, 2-ketoglutaric acid, and the like), hexanedioic acid and substituted variants (e.g., mucic acid), butenedioic acid (both cis and trans isomers), iminodiacetic acid, phthalic acid, and the like; triprotic acids such as citric acid, 2-methylpropane-1,2,3-tricarboxylic acid, benzenetricarboxylic acid, nitrilotriacetic acid, and the like; tetraprotic acids such as prehnitic acid, pyromellitic acid, and the like; and even higher degree acids (e.g., penta-, hexa-, heptaprotic, etc.). Where a tri-, tetra-, or higher acid is used, one or more of the carboxyl protons can be replaced by cationic atoms or groups (e.g., alkali metal ions), which can be the same or different.

In certain embodiments, preference can be given to those organic acids or bases which are, or can be made to be, highly soluble in aqueous systems; acids that include groups that enhance solubility in water (e.g., hydroxyl groups), examples of which include tartaric acid, citric acid, and citramalic acid, can be preferred in some circumstances. Example of these bases include NaOH, $Na_2CO_3$, and $NH_3$. In these and/or other embodiments, preference can be given to those organic acids and bases which are biocompatible; many of the organic acids and bases listed above are used in preparing or treating food products, personal care products, and the like. Alternatively or additionally, preference can be given to those organic acids and bases which can act to chelate the metallic cations involved in crosslinking the macromolecular matrix of the biofilm.

Basic forms of the present composition generally have a pH greater than ~7.5, generally greater than 8.0, greater than 8.4, greater than 8.6, greater than 9.0, greater than 9.2, greater than 9.4, greater than 9.6 greater than 9.8, greater than 10.0, greater than 10.2, greater than 10.4, greater than 10.6, greater than 10.8, greater than 11.0, greater than 11.2, greater than 11.4, greater than 11.6, greater than 11.8, greater than 12.0, greater than 12.2, greater than 12.4, or even greater than 12.5. In terms of ranges, the pH can be from ~8 to ~12.5, from ~8.2 to ~12.0, from ~8.4 to ~11.5, from ~8.6 to ~11.0, or from ~8.8 to ~10.5.

Basicity is achieved by adding one or more bases such as, but not limited to, alkali metal salts of weak acids, including acetates, bicarbonates, fulmates, lactates, phosphates, and glutamates; alkali metal nitrates; alkali metal hydroxides, in particular NaOH and KOH; alkali earth metal hydroxides, in particular Mg(OH)$_2$; alkali metal borates; NH$_3$; and alkali metal hypochlorites (e.g., NaClO) and bicarbonates (e.g., NaHCO$_3$).

The amount of acid or base added to the solvent component can be calculated or can be added until the composition reaches a desired pH, using standard pH monitoring equipment to track increases or decreases.

In the compositions described in US Patent Publ. Nos. 2010/0086576 and 2012/059263, which were not intended to include one or more organic liquids as part of the solvent component, inclusion of a surfactant, preferably an ionic surfactant, is required. In the present composition, surfactant is not required, although inclusion of a surfactant can increase the ability to both solubilize EPS polymers (by binding to those polymers and bringing them into solution) and by helping to extract proteins from bacterial cell walls, leading to cell leakage and lysis.

Essentially any material having surface active properties in water can be employed, regardless of whether water is present in the solvent component of the composition, although those that bear some type of ionic charge are expected to have enhanced antimicrobial efficacy because such charges, when brought into contact with a bacteria, are believed to lead to more effective cell membrane disruption and, ultimately, to cell leakage and lysis. This mechanism can kill even sessile bacteria because it does not involve or entail disruption of a cellular process.

Polar surfactants generally are more efficacious than non-polar surfactants. Ionic surfactants are most effective because they can directly interact with EPS polymers and bacterial cell wall proteins. For polar surfactants, cationic surfactants are the most effective, followed by zwitterionic and anionic surfactants. Additionally, smaller surfactants are more efficacious because they can more easily move through the biofilm macromolecular matrix and access the entrained bacteria. Another factor which influences the efficacy of ionic surfactants is the size of side-groups attached to the polar head. Larger size-groups and more side-groups on the polar head can decrease the efficacy of surfactants.

Because surfactant is not the only component in the present composition involved in solubilizing proteins (i.e., solvent assists in this process), non-ionic surfactants can find more utility in the present composition than in prior compositions which did not contain solvent. Bacterial cell wall proteins already are solubilized by organic liquid(s) in the solvent component, allowing the non-ionic surfactants to interact with them by lower-order mechanisms such as Van der Waals forces.

Because surfactants often provide tangential advantages, they can be included in the composition even where they yield little or no improvement in efficacy above that afforded by the organic liquid(s).

Potentially useful anionic surfactants include, but are not limited to, ammonium lauryl sulfate, dioctyl sodium sulfosuccinate, perflourobutanesulfonic acid, perfluorononanoic acid, perfluorooctanesulfonic acid, perfluorooctanoic acid, potassium laurylsulfate, sodium dodecylbenzenesulfonate, sodium laureth sulfate, sodium lauroyl sarcosinate, sodium myreth sulfate, sodium pareth sulfate, sodium stearate, sodium chenodeoxycholate, N-lauroylsarcosine sodium salt, lithium dodecyl sulfate, 1-octanesulfonic acid sodium salt, sodium cholate hydrate, sodium deoxycholate, sodium dodecyl sulfate (SDS), sodium glycodeoxycholate, sodium lauryl sulfate, and the alkyl phosphates set forth in U.S. Pat. No. 6,610,314.

Potentially useful cationic surfactants include, but are not limited to, cetylpyridinium chloride (CPC), cetyl trimethylammonium chloride, benzethonium chloride, 5-bromo-5-nitro-1,3-dioxane, dimethyldioctadecylammonium chloride, cetrimonium bromide, dioctadecyl-dimethylammonium bromide, tretadecyltrimethyl ammonium borine, benzalkonium chloride (BK), hexadecylpyridinium chloride monohydrate and hexadecyltrimethylammonium bromide, with the benzalkonium chloride being a preferred material.

Potentially useful nonionic surfactants include, but are not limited to, sodium polyoxyethylene glycol dodecyl ether, N-decanoyl-N-methylglucamine, digitonin, n-dodecyl β-D-maltoside, octyl β-D-glucopyranoside, octylphenol ethoxylate, polyoxyethylene (8) isooctyl phenyl ether, polyoxyethylene sorbitan monolaurate, and polyoxyethylene (20) sorbitan cholamidopropyl] dimethylammonio]-2-hydroxy-1-propane sulfonate, 3-[(3-cholamidopropyl) dimethylammonio]-1-propane sulfonate, 3-(decyldimethylammonio) propanesulfonate inner salt, and N-dodecyl-N,N-dimethyl-3-ammonio-1-propanesulfonate.

Potentially useful zwitterionic surfactants include sulfonates (e.g. 3-[(3-cholamidopropyl)dimethylammonio]-1-propanesulfonate), sultaines (e.g. cocamidopropyl hydroxysultaine), betaines (e.g. cocamidopropyl betaine), and phosphates (e.g. lecithin).

For other potentially useful materials, the interested reader is directed to any of a variety of other sources including, for example, U.S. Pat. Nos. 4,107,328 and 6,953,772 as well as U.S. Pat. Publ. No. 2007/0264310.

When a surfactant is included in a formulation, the amount can vary widely based on a variety of factors including, but not limited to, the age of the biofilm (particularly whether it is entrenched, a factor which relates to the type of proteins and mass of the macromolecular matrix), size of the biofilm, amount of surface soiling, the species of bacteria, whether more than one type of bacteria is present, and the solubility of the surfactant(s).

The amount of surfactant generally constitutes greater than ~0.02%, typically at least ~0.04%, typically at least ~0.06%, typically at least ~0.08%, and typically at least ~0.10% (all w/w, based on the total weight of the composition). Some compositions can include even more surfactant, for example, at least ~0.12%, at least ~0.13%, at least ~0.14%, at least ~0.15%, at least ~0.16%, at least ~0.2%, at least ~0.25%, at least ~0.5%, at least ~0.75%, and even at least 1% of the composition (all w/w, based on the total weight of the composition). The upper limit of amount of surfactant to be incorporated can be defined by the solubility limits of the particular surfactant(s) chosen. (Any two of the foregoing minimum amounts can be combined to provide an exemplary range of amounts of surfactant.)

At times, maximum amounts of certain types of surfactants that can be present in a composition for a particular end use (without specific testing, review and approval) are set by governmental regulations. For example, compositions intended for food contact without rinsing can have a maximum amount of 0.02% (by wt.) BK, compositions intended for use as oral rinsing can have a maximum amount of 0.1% (by wt.) CPC (although an additional 0.13% (by wt.) BK can be present as a preservative), and compositions intended for application to compromised or uncompromised skin can have a maximum amount of 0.13% (by wt.) BK, while compositions involved in applications such as sterilizing medical instruments can include at least 1% (by wt.), often up to ~2% (by wt.) or more of any of a variety of surfactants.

The antimicrobial composition can include a variety of additives and adjuvants to make it more amenable for use in a particular end-use application without negatively affecting its efficacy in a substantial manner. Examples include, but are not limited to, emollients, fungicides, fragrances, pigments, dyes, defoamers, foaming agents, flavors, abrasives, bleaching agents, preservatives (e.g., antioxidants) and the like. A comprehensive listing of additives approved by the U.S. Food and Drug Administration is available (by hyperlink to a zipped text file) at http://www.fda.gov/Drugs/InformationOnDrugs/ucm113978.htm (link active as of filing date of this application).

The composition does not require inclusion of an active antimicrobial agent for efficacy, but such materials can be included in certain embodiments. Non-limiting examples of potentially useful active antimicrobial additives include $C_2$-$C_8$ alcohols (other than or in addition to any used as an organic liquid of the solvent component) such as ethanol, n-propanol, and the like; aldehydes such as gluteraldehyde, formaldehyde, and o-phthalaldehyde; formaldehyde-generating compounds such as noxythiolin, tauroline, hexamine, urea formaldehydes, imidazolone derivatives, and the like; anilides, particularly triclocarban; biguanides such as chlorhexidine and alexidine, as well as polymeric forms such as poly(hexamethylene biguanide); dicarboximidamides (e.g., substituted or unsubstituted propamidine) and their isethionate salts; halogen atom-containing or releasing compounds such as bleach, $ClO_2$, dichloroisocyanurate salts, tosylchloramide, iodine (and iodophors), and the like; silver and silver compounds such as silver acetate, silver sulfadiazine, and silver nitrate; peroxides such as $H_2O_2$ and peracetic acid; phenols, bis-phenols and halophenols (including hexachlorophene and phenoxyphenols such as triclosan); and quaternary ammonium compounds. Additionally, antibiotics may be added for medical applications.

Based on the foregoing description, one can see that the non-solvent portion of the composition can consist of, or consist essentially of, solutes (particularly those deriving from a buffer precursor, either alone or in combination with other solutes) and ions resulting from dissociation of an acid or base. In other embodiments, the non-solvent portion can consist of, or consist essentially of, solutes, ions resulting from dissociation of an acid or base, and one or more surfactants. In yet other embodiments, the non-solvent portion can consist of, or consist essentially of, solutes, ions resulting from dissociation of an acid or base, one or more surfactants and less than 1% w/v bleach solution.

The composition conveniently can be provided as a solution, as a ready-to-use product or as a concentrate, although other forms might be desirable for certain end-use applications. Accordingly, the composition can provided as a soluble powder (for subsequent dilution, an option which can reduce transportation costs), a slurry, or a thicker form such as a gel or paste which might be particularly useful for providing increased residence times.

The composition can also be provided as a gel or coating that actively elutes out to disinfect or prevent colonization of a surface.

In a gel, a liquid form of the composition can be formulated into an oleaginous, absorption, water/oil emulsion, oil/water emulsion, or water-miscible carrier base. Examples of oleaginous bases include white petrolatum and white ointment bases. Examples of absorption bases include hydrophilic petrolatum, anhydrous lanolin, and those used in such commercial products as Aquabase™, Aquaphor™, and Polysorb™ ointments. Water/oil bases can include cold-cream type bases, hydrous lanolin, and those used in such commercial products as Hydrocream™, Eucerin™, and Nivea™ moisturizers. Oil/water bases can include hydrophilic ointment as well as those used in such commercial products as Dermabase™, Velvachol™, and Unibase™ ointments. Water-miscible bases include PEG ointment, cellulosic gels, chitosan gels, polyvinyl pyrollidone, and those used in such commercial products as Polybase™ ointment.

Examples of solvent-containing compositions that can be provided as stable gels are shown in Table 3. (By "stable" is meant no substantial loss in efficacy or change in appearance after room temperature storage for several months.) Each had an effective pH of 4.0 and an osmolarity of 2.33 Osm/L; the first two had 10% w/v entrained solvent (DGME and IPA, respectively), while the third had 1% w/v entrained phenoxyethanol (because U.S. Food and Drug Administration regulations permit far less of this material in compositions intended for dermal contact).

TABLE 3

| Gel-form compositions (% by wt.) | | | |
|---|---|---|---|
| | #1 | #2 | #3 |
| PEG 400 | 45 | 45 | 45 |
| PEG 3350 | 30 | 30 | 30 |
| BK | 0.14 | 0.14 | 0.14 |
| sodium citrate dihydrate | 3.57 | 3.57 | 3.57 |
| citric acid | 3.41 | 3.41 | 3.41 |
| solvent | 2.5 | 2.5 | 0.25 |
| water | 15.39 | 15.39 | 17.64 |

Coatings can be formulated from the gel forms above or can be incorporated into more adherent and stable products, such as latex, silicone, polyurethane, cross-linked PEG, chitosan gels, or a coalescent such as polyvinyl pyrollidone.

Regardless of the physical form of the composition, increasing temperature and/or agitation during application treatment can beneficially impact total disinfection as well as disinfection rate. Because the compositions dissolve and/or break up the macromolecular matrix and extracting bacterial cell wall proteins, applying the composition in a flowing manner can be beneficial, i.e., partially or fully solvated EPS macromolecules can be removed from the treatment area, preventing it from blocking treatment chemicals, and fresh composition can be introduced to the bacterial cell walls.

The composition can be employed in a variety of ways. For example, when used to treat a biofilm on a surface (e.g., cutting board, counter, desk, etc.), the composition can be applied directly to the biofilm, optionally followed by physical rubbing or buffing, or the composition can be applied to the rubbing/buffing medium, e.g., cloth. Where a biofilm in an inaccessible area is to be treated, soaking or immersion of the biofilm in an excess of the composition can be performed for a time sufficient to essentially solvate the biofilm, which then can be flushed from the affected area. Regardless of contact method, the surfactant component(s) are believed to kill significant numbers of bacteria without a need for the bacteria to be removed from the biofilm or vice versa. The solution may applied by a number of means including spraying onto or allowed to flow over a surface, applied with or without pressure, applied with soaked wipes or bandages, or applied ultrasonically.

Compositions according to the present invention are more efficacious, both in terms of total number of bacterial killed and of speed (amount of time needed to achieve an acceptable amount of bacterial reduction), than otherwise equivalent compositions that do not contain organic liquid(s) in the solvent component; this is true even where the amount of surfactant component is greatly reduced or even omitted. Thus, a composition having a solvent component with a $\delta_p$ value of ~15.5 will, under the same testing conditions, increase the amount of reduction of *P. aeruginosa* by 1 to 3 log and of *S. aureus* by 1 to 2 log relative to an aqueous composition having a $\delta_p$ value of 16.0; a composition having a solvent component with a $\delta_p$ value of ~15.0 (i.e., 14.9-15.2) will have even greater increases in efficacy, e.g., on the order of 3 to 6 log for *P. aeruginosa* and of 2 to 3 log for *S. aureus*. A graphical depiction of the impact of the $\delta_p$ value of the solvent component on efficacy can be seen in, for example, FIG. 6.

Due to the abundance of microbial contaminations, the present composition has a large number of potential uses including, but not limited to the cleaning of residential, commercial and industrial hard surfaces such as bathroom surfaces (floors, countertops, sinks, drains including floor and sink and shower, toilet bowls, toilet seats, showers including walls, floors, tubs, shower curtains and shower doors, fixtures, and the like), kitchen surfaces (such as countertops, floors, stovetops, sinks and drains, cutting boards, pots, pans, dishes, eating utensils, cooking and serving utensils, dishwasher internal surfaces, food processing equipment of all types, coffee makers, icemakers, and the like), industrial food processing surfaces such as for meat, poultry, seafood, dairy, produce and beverage processing (such as floors, drains, cutting and preparation surfaces, packaging surfaces, processing equipment holding tanks, cabinets, and surfaces transfer belts fluid lines chambers, and the like), and food surfaces directly by immersion spray or other means such as animal carcasses, individual cuts, egg washing, and produce washing.

The present composition also can be used in the preparation, cleaning and/or disinfection of medical/healthcare surfaces such as surgical theater objects (e.g., tables, trays, floors, walls, sinks, drains, any instruments and tools, implants and devices before installation or being treated in the body during surgery); respirators; reprocessing of devices like scopes of various types (e.g., endoscopes, gastroscopes, laparoscopes, etc.); dialysis machines; analyzers of all types such as for blood, urine, or other tissue/fluid samples; reprocessing of implants or surgical tools, especially heat sensitive where autoclaving can cause issues but also as a final sterilization before surgical use; patient care surfaces including but not limited to floors, walls, sinks, fixtures, toilets, drains, bed rails and frames, telephone, audio-visual remote controllers, tables, chairs, etc.; cleaning of contact lenses, and cleaning of dentures.

Biofilms and biofouling greatly decrease the energy efficiency of production processes by a number of mechanisms, including increasing surface friction, degrading metallic components, clogging fluid lines, coating surfaces and decreasing heat transfer rates. The present composition can counteract such deleterious effects in industrial applications such as cleaning and/or preparing chemical reactors; processing or repackaging equipment, especially where contamination creates a need for repeated maintenance; treatment of surfaces where biofouling causes corrosion or reduced heat transfer characteristics detrimental to function; and oil and gas production for the production and pumping equipment, downhole applications (e.g., to control biofouling that impedes or reduces production), as well as anywhere that bacterial contamination creates vapor issues or chemical changes, e.g. bacterial growth in biodiesel and "souring" of gas during storage.

Other surfaces that can benefit from applications of the present composition, regardless of form, include toys, baby pacifiers, door handles, grocery carts, telephones, remote control devices, the drums of washing machines, humidifiers, dehumidifiers, air conditioning condensers, automotive ductwork, air handling ductwork, garbage cans, reverse osmosis filter elements, and ion exchange filter elements.

Other potential applications for the present composition include treatment of textiles and fabrics such as general clothes washing especially for malodor, hospital linen for disinfection or sanitization, baby laundry for disinfection or sanitization, and bandages; treatment of living human or animal tissue such as for treating rhinosinusitis (either directly clearing the sinus cavity or combined with a packing material), otitis, surgical site prep, surgical wash, rinsing of surgical sites during operation or before, inclusion in the body to remain after closure to provide extended antibacterial protection especially when provided as a gel form within a surgical site directly or when left to surround an implant or implanted device such as a pacemaker, treatment of wounds either as a wash as a gel intended to be left for an extended period on the wound or intended for use as a treatment solution as in negative pressure wound therapy devices, treatment of cystic fibrosis to remove biofilm from the lungs, treatment of tonsils and adenoids, as an antibacterial hemostat when combined with a suitable clotting agent, oral care as a rinse or toothpaste, rinsing of impacted teeth after root canals, toe fungus, yeast infections, diaper rash, acne, hand sanitizer, skin cleanser, for treatment of udder rot, hoof rot, metritis, dairy teat dip, and the like; and flow channel-type devices such as dental unit water lines, re-circulating cooling/heating loops (either open or closed) such as in cooling towers, heat exchangers, manufacturing equipment or laboratory equipment, re-circulating loops for lubricants and cutting fluids, processing equipment such as chemical reactors, fermenting tanks, liquid and beverage packaging, any system that may contain any or all of holding tanks, fluid transfer lines, valves, joints or dispensers for aqueous based systems, condensate collection and transfer lines, vapor lines especially where water vapor is present, and tanker transports such as in over the road trucking or rail.

While various embodiments of the present invention have been provided, they are presented by way of example and not limitation. The following claims and their equivalents define the breadth and scope of the inventive methods and compositions, and the same are not to be limited by or to any of the foregoing exemplary embodiments.

To assist in understanding the foregoing description, the following definitions that are intended to apply throughout (unless the surrounding text explicitly indicates a contrary intention):

"microbe" means any type of microorganism including, but not limited to, bacteria, viruses, fungi, viroids, prions, and the like;

"antimicrobial agent" means a substance having the ability to cause greater than a 90% (1 log) reduction in the number of one or more microbes;

"active antimicrobial agent" means an antimicrobial agent that is effective only or primarily during the active parts of the lifecycle, e.g., cell division, of a microbe;

"biofilm" means a community of microbes, particularly bacteria and fungi, attached to a surface with the community members being contained in and/or protected by a self-generated macromolecular matrix;

"entrenched biofilm" is a biofilm that has reached a steady state mass after a growth period of two or more days;

"buffer" means a compound or mixture of compounds having an ability to maintain the pH of a solution to which it is added within relatively narrow limits;

"buffer precursor" means a compound that, when added to a mixture containing an acid or a base, results in a buffer;

"polyacid" means a compound having at least two carboxyl groups and specifically includes dicarboxylic acids, tricarboxylic acids, etc.;

"benzalkonium chloride" refers to any compound defined by the following general formula

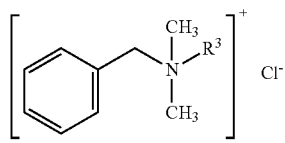

(IV)

where $R^3$ is a $C_8$-$C_{18}$ alkyl group, or any mixture of such compounds;

"residence time" means the amount of time that an antimicrobial agent is allowed to contact a bacterial biofilm;

"biocompatible" means presenting no significant, long-term deleterious effects on or in a mammalian species;

"biodegradation" means transformation, via enzymatic, chemical or physical in vivo processes, of a chemical into smaller chemical species;

"biosorption" means absorption of a material into the body of a mammalian species;

"absorption base" is a blend of an oleaginous base and one or more surfactants;

"bleach solution" is an aqueous composition that contains from ~4.0% to ~6.5% (by wt.) hypochlorite ion and has a 10≤pH≤12;

"soil load" means a solution of one or more organic and/or inorganic substances added to the suspension of a test organism to simulate the presence of body secretions, excretions, and the like;

"inoculum" means a solution containing bacteria, growth solution (e.g., tryptic soy broth) and protein soil load; and "substituted" means one containing a heteroatom or functionality (e.g., hydrocarbyl group) that does not interfere with the intended purpose of the group in question.

EXAMPLES

The following examples employ a number of tests to evaluate various antimicrobial compositions against bacteria in a variety of formats. Brief descriptions of these tests follow:

Quantitative carrier test (QCT), ASTM test method E2197-02 (§ 9): To three separate vessels, each containing 10 mL KH₂PO₄ solution (~30% w/v in water), are added, respectively, 0.5 g tryptone, 0.5 g bovine serum albumen, and 0.04 g bovine mucin; each was sterilized separately. In a separate container, 340 μL microbial suspension (bacteria grown from a suspension originally obtained from ATCC of Manassas, Va.), 25 μL of the BSA solution, 100 μL of the mucin solution, and 35 μL of the tryptone stock are added together to provide a soil loaded bacterial suspension which is used immediately after preparation. A 10 μL aliquot of the soil loaded bacterial suspension is applied to a clean stainless steel disk and allowed to dry before a 50 μL aliquot of antimicrobial composition is applied. Results of this test are reported as reductions from control (logarithmic scale).

Biofilm CDC reactor test, ASTM E2871-12: Biofilms are grown on coupons in a CDC reactor (ASTM E-2562). Upon removal, the coupons are immersed in sterile buffered water to remove planktonic bacteria before being placed in sterile 50 mL conical tubes and having 4 mL antimicrobial composition added thereto. After a specified dwell time (e.g., 3, 5 or 10 minutes), 36 mL of a Day/Engler broth (available from a variety of commercial sources such as Sigma-Aldrich) is added to the tube to stop any further antimicrobial activity of the composition, and the remaining bacterial load is quantified. Results are reported as reductions from control (logarithmic scale).

Planktonic bacteria test (AOAC 955.14, 955.15, 964.02): A soil load (~$10^6$ suspended bacteria) is applied to a number of Peni cylinders (typically 60), which are placed in sterile test tubes containing 10 mL of an antimicrobial composition. After the treatment time (e.g., 3, 5 or 10 minutes), the cylinders are transferred to test tubes containing growth media, a neutralizer (e.g., Day/Engler broth), and a growth indicator such as a pH-sensitive dye that changes color if the pH drops below neutral (as would happen during cell respiration by any bacteria living on the Peni cylinder after treatment). Visual color inspection is performed, with results being provided as an amount of time (in seconds) required to completely disinfect a tested surface. (Where 60 test cylinders are run, 58 must lack the color change to achieve a passing result.)

After precursor buffering compositions A through M from Table 4 were prepared, 37% (by wt.) HCl or 50% (by wt.) NaOH was added to achieve the target pH.

Examples 1-24

Twenty four antimicrobial compositions were prepared: examples 1-8 contained 1.78 g (0.008 mol) SDS anionic surfactant, examples 9-16 contained 2.10 g (0.008 mol) BK cationic surfactant, and examples 17-24 contained no added surfactant.

All these compositions were prepared so as to have effective solute concentrations of 2.33 Osm/L, with half of the compositions from each of the three groups being acidic (pH=4.0) and the other half being alkaline (pH=10.0):

acidic (examples 1-4, 9-12 and 17-20)—127.0 g/L citric acid and 112.5 g/L sodium citrate dihydrate, and alkaline (examples 5-9, 13-16 and 21-24)—19.4 g/L NaOH and 65.0 g/L KH₂PO₄.

Each composition was prepared in a 100 mL glass vessel by adding surfactant (if used) with sufficient water to disperse it, the buffer precursor (salt), and then the acid or base.

To each of the compositions of examples 1-4 was added, respectively, 10 g of one of the following organic liquids (with the parenthetical numbers being the $\delta_p$ values, in $MPa^{1/2}$, of the solvent components of the resulting compositions): PGME (14.96), DGME (15.32), IPA (15.01) or DMSO (16.04). Sufficient water then was added to bring each composition to 100 mL before the vessel was covered and stored at room temperature (~23° C.).

The foregoing solvent and water addition was repeated for the compositions of the other groups, i.e., examples 5-8, 9-12, 13-16, 17-20 and 21-24.

The compositions are summarized below in Table 4.

TABLE 4

Antimicrobial compositions from
Examples 1-24 (all 2.33 Osm/L)

|    | Surfactant | pH   | Solvent |
|----|------------|------|---------|
| 1  | anionic    | 4.0  | PGME    |
| 2  | anionic    | 4.0  | DGME    |
| 3  | anionic    | 4.0  | IPA     |
| 4  | anionic    | 4.0  | DMSO    |
| 5  | anionic    | 10.0 | PGME    |
| 6  | anionic    | 10.0 | DGME    |
| 7  | anionic    | 10.0 | IPA     |
| 8  | anionic    | 10.0 | DMSO    |
| 9  | cationic   | 4.0  | PGME    |
| 10 | cationic   | 4.0  | DGME    |
| 11 | cationic   | 4.0  | IPA     |
| 12 | cationic   | 4.0  | DMSO    |
| 13 | cationic   | 10.0 | PGME    |
| 14 | cationic   | 10.0 | DGME    |
| 15 | cationic   | 10.0 | IPA     |
| 16 | cationic   | 10.0 | DMSO    |
| 17 | none       | 4.0  | PGME    |
| 18 | none       | 4.0  | DGME    |
| 19 | none       | 4.0  | IPA     |
| 20 | none       | 4.0  | DMSO    |
| 21 | none       | 10.0 | PGME    |
| 22 | none       | 10.0 | DGME    |
| 23 | none       | 10.0 | IPA     |
| 24 | none       | 10.0 | DMSO    |

These compositions were evaluated in a number of experiments to assess their effectiveness against planktonic bacteria, soil-loaded bacteria, and biofilm-form bacteria. Results of testing of these compositions are summarized below in Table 5, where "SA" represents *S. aureus*, "PA" represents *P. aeruginosa* and "EC" represents *E. coli*.

TABLE 5

Antimicrobial efficacy of compositions from Table 4

|    | Planktonic, time to disinfection (sec) | | | QCT, log reductions | | Biofilm, log reductions | |
|----|------|------|------|------|------|------|------|
|    | SA   | PA   | EC   | SA   | PA   | SA   | PA   |
| 1  | 60   | 15   | 15   | 5.00 | 5.00 | 3.30 | 3.77 |
| 2  | 60   | 60   | 120  | 1.73 | 2.50 | 0.97 | 2.04 |
| 3  | >60* | 30   | 120  | 2.75 | 1.30 | 2.01 | 2.34 |
| 4  | >60* | 60   | 120  | 1.57 | 3.60 | 0.71 | 1.51 |
| 5  | >60* | 120  | 15   | 1.06 | 2.50 | 2.13 | 1.87 |
| 6  | >60* | 60   | 120  | 1.70 | 2.00 | 0.00 | 1.94 |
| 7  | >60* | 15   | 120  | 1.96 | 0.00 | 1.36 | 2.01 |
| 8  | >60* | 120  | 120  | 1.97 | 0.00 | 0    | 1.16 |
| 9  | 15   | 15   | 15   | 5.28 | 3.00 | 3.60 | 6.96 |
| 10 | 15   | 15   | 15   | 2.56 | 5.00 | 1.78 | 2.04 |
| 11 | 15   | 15   | 15   | 5.17 | 1.06 | 2.12 | 3.89 |
| 12 | 15   | 30   | 15   | 1.55 | 2.99 | 1.14 | 2.23 |
| 13 | 15   | 15   | 60   | 4.30 | 4.50 | 1.20 | 4.93 |
| 14 | 15   | 15   | 30   | 1.24 | 2.96 | 1.19 | 2.63 |
| 15 | 15   | 15   | 30   | 2.09 | 6.00 | 0.76 | 3.81 |
| 16 | 15   | 15   | 30   | 2.50 | 3.03 | 2.24 | 1.08 |
| 17 | >60* | 30   | 30   | 4.95 | 3.00 | 2.62 | 5.18 |
| 18 | >60* | 15   | 120  | 1.72 | 5.00 | 0.06 | 2.44 |
| 19 | 60   | 60   | 90   | 2.15 | 0.00 | 0.88 | 2.64 |
| 20 | 30   | 30   | 120  | 1.26 | 1.42 | 0    | 1.83 |
| 21 | 15   | 120  | 30   | 2.05 | 4.35 | 1.97 | 3.60 |
| 22 | 15   | 120  | 200  | 1.24 | 3.50 | 0    | 0.81 |
| 23 | >60* | 120  | 200  | 1.38 | 0.50 | 0.33 | 1.51 |
| 24 | >60* | 120  | 120  | 5.00 | 5.00 | 0.13 | 0.54 |

*S. aureus was not tested beyond 60 seconds, even if disinfection was not achieved.

Figure 1B:
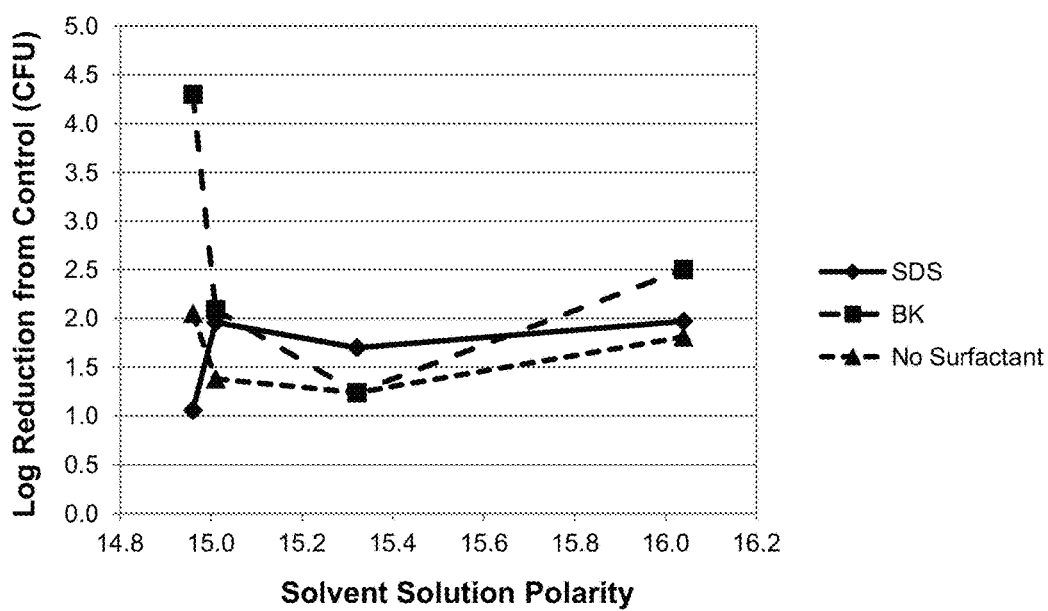
Figure 2A:
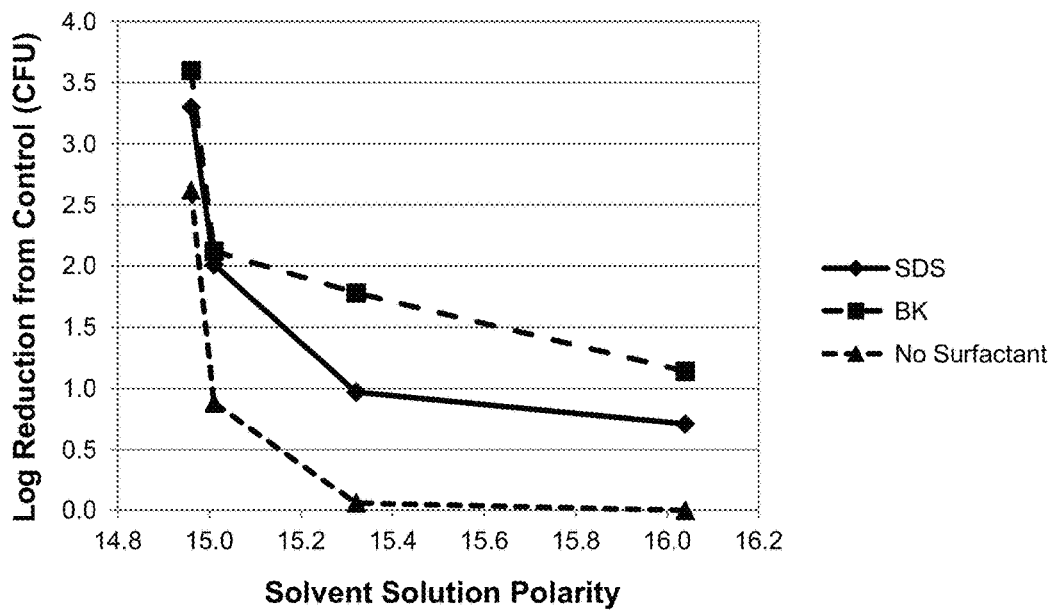
FIGS. 2a and 2b depict CDC reactor (biofilm) testing results for compositions at pH=4 and pH=10, respectively, employing anionic surfactant, cationic surfactant, and no surfactant, with S. aureus bacterial reductions plotted against $\delta_p$ values of the solvent component of antimicrobial compositions.
Figure 2B:
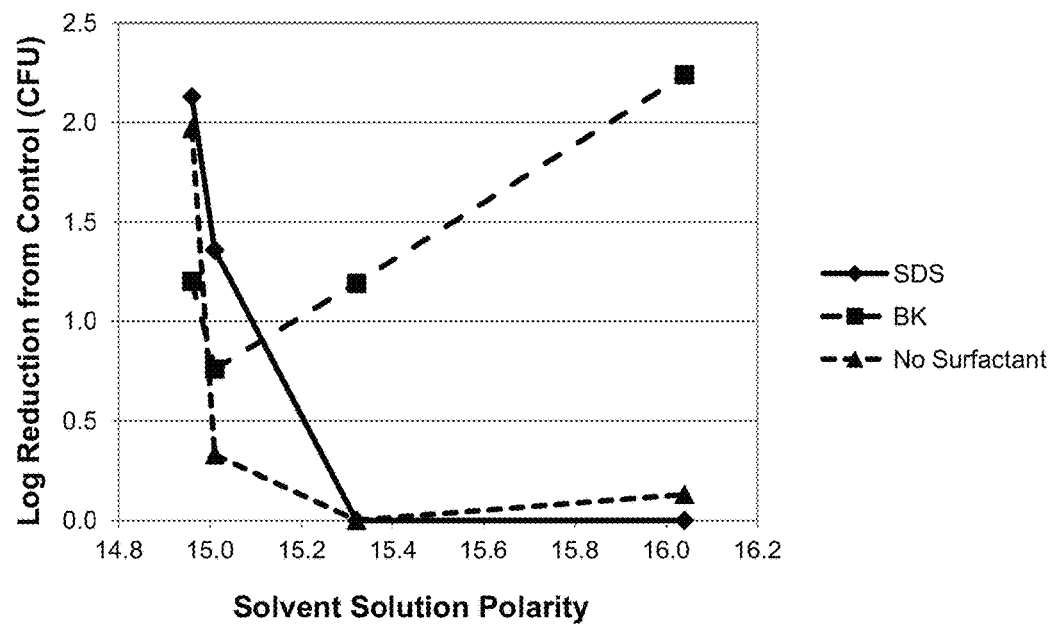
Figure 3A:
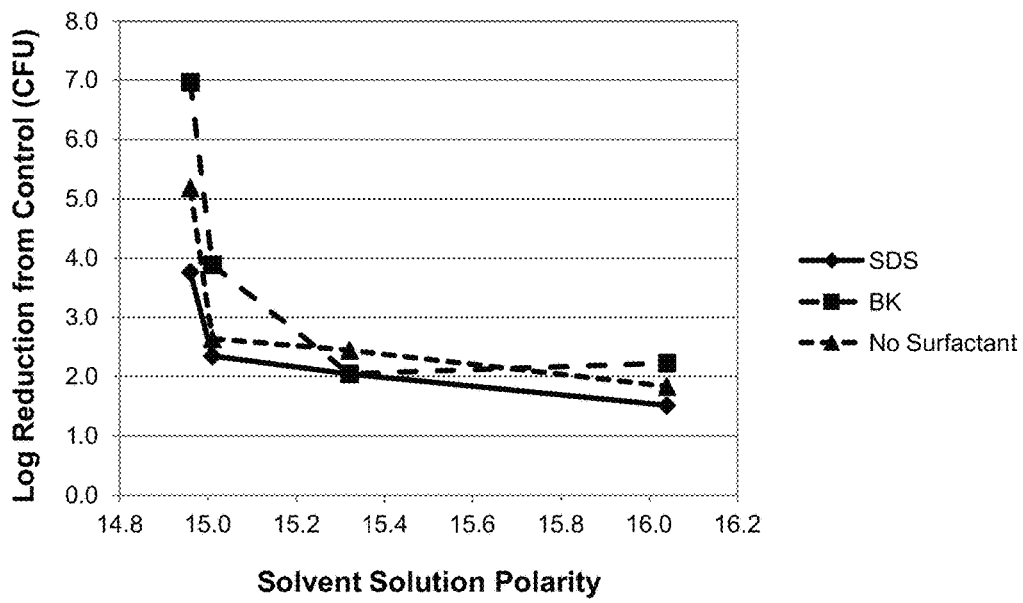
FIGS. 3a and 3b depict CDC reactor (biofilm) testing results for compositions at pH=4 and pH=10, respectively, employing anionic surfactant, cationic surfactant, and no surfactant, with P. aeruginosa bacterial reductions plotted against $\delta_p$ values of the solvent component of antimicrobial compositions.
Figure 3B:
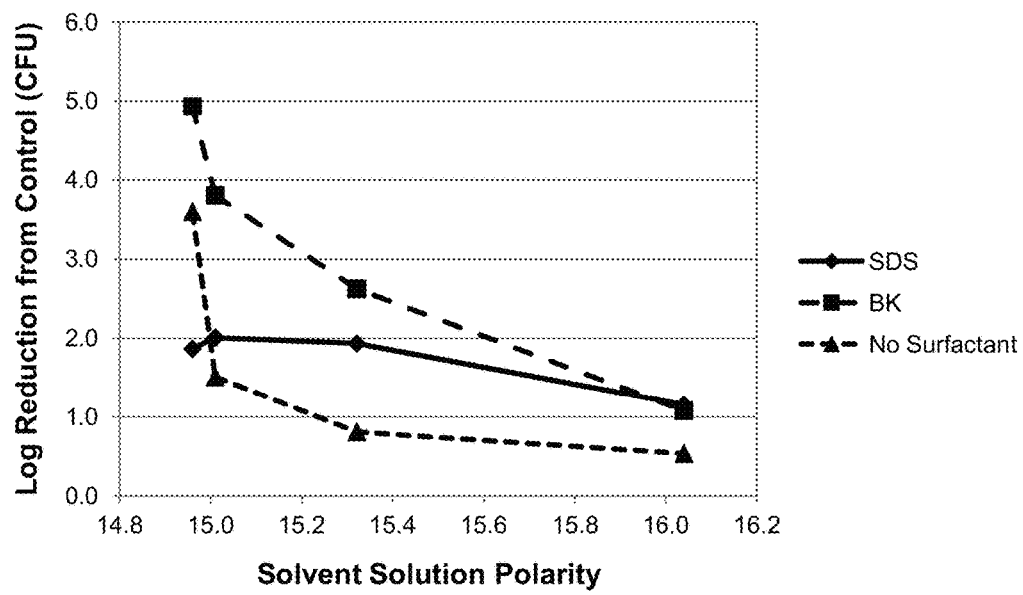

Bacterial reduction versus $\delta_p$ values of the solvent component of the compositions were plotted, with the results being shown as follows:

FIG. 1a—*S. aureus* QCT data, pH=4 composition
FIG. 1b—*S. aureus* QCT data, pH=10 composition
FIG. 2a—*S. aureus* CDC reactor (biofilm), pH=4 composition
FIG. 2b—*S. aureus* CDC reactor (biofilm), pH=10 composition
FIG. 3a—*P. aeruginosa* CDC reactor (biofilm), pH=4 composition
FIG. 3b—*P. aeruginosa* CDC reactor (biofilm), pH=10 composition In each of these plots, a definite increase in efficacy can be seen when the $\delta_p$ value falls below about 15.2 MPa$^{1/2}$. The exact point where the discontinuity begins varies somewhat between the planktonic bacteria and biofilm tests, but the transition occurs at $15.2 \leq \delta_p \leq 15.4$ MPa$^{1/2}$.

Further, the plots for *S. aureus* at pH=10 with cationic surfactant (FIGS. 1b and 2b) indicate efficacy beyond the theoretical bound. Without wishing to be bound by theory, a different (sub)section of the proteins on the wall of this bacteria might be solubilized at the $\delta_p$ value corresponding to the anomalous log reduction data point.

The data from Table 5 also seem to indicate that pH=4 compositions generally are somewhat more effective than pH=10 compositions and that cationic surfactant-containing compositions are more effective than anionic surfactant-containing and surfactant-free counterparts, although the latter still demonstrated significant antimicrobial capability.

After the foregoing testing was completed, the correlation of each of the HSPs to the results was evaluated. Basic regression analysis was performed for the results of each individual parameter and for the interaction radius value. The fit and probabilty results for this regression analysis are shown below in Table 6.

TABLE 6

Regression analysis results for Table 5 data

|             | S. aureus | | P. aeruginosa | |
|-------------|---------|---------|---------|---------|
|             | F-value | p-value | F-value | p-value |
| $\delta_d$  | 5.27    | 0.0320  | 11.43   | 0.003   |
| $\delta_p$  | 6.01    | 0.0230  | 12.34   | 0.002   |
| $\delta_h$  | 0.15    | 0.7020  | 0.74    | 0.399   |
| $\delta_{dp}$ | 5.86  | 0.0240  | 12.19   | 0.002   |
| $R_a$       | 5.35    | 0.0300  | 6.78    | 0.016   |

The foregoing data indicate that the $\delta_p$ parameter has the highest fit and lowest p-value for *S. aureus* and *P. aeruginosa*. (For the solutions evaluated herein, the $\delta_d$ and $\delta_p$ parameters follow the same trends when placed into solution. As such, strong correlation between these parameters will exist when a regression is performed versus efficacy. Accordingly, the $\delta_d$ value is also expected to be useful in formulating compositions and, in that case, the point of delimination for solution efficacy will be functionally equivalent to the $\delta_p$ value-derived compositions.)

Examples 25-32

The composition preparation procedure from Examples 1-24 was repeated, with the following differences (all employed 2.1 g/L BK as surfactant):
examples 25-26—19.0 g/L NaOH, 66.0 g/L KH$_2$PO$_4$ (pH=7.5 and 2.33 Osm/L),
examples 27-28—9.7 g/L NaOH, 32.5 g/L KH$_2$PO$_4$ (pH=10.0 and 1.165 Osm/L),
examples 29-30—63.5 g/L citric acid, 56.3 g/L sodium citrate dihydrate (pH=4.0 and 1.165 Osm/L), and examples 31-32—19.4 g/L NaOH, 65.0 g/L KH$_2$PO$_4$ (pH=10.0 and 2.33 Osm/L).

Varying amounts of organic liquids were added to yield the compositions shown in Table 7, which then were subjected to biofilm CDC reactor tests. (All compositions had 15 second time-to-disinfection in planktonic testing.)

TABLE 7

Tested compositions and biofilm testing results

| | Solvent | | $\delta_p$ | Biofilm, log reduction | |
|---|---|---|---|---|---|
| | Identity | g/L | (MPa$^{1/2}$) | S. aureus | P. aeruginosa |
| 25 | PGME | 100 | 14.96 | 2.33 | 4.65 |
| 26 | IPA | 100 | 15.01 | 2.54 | 3.81 |
| 27 | PGME | 100 | 14.96 | 3.07 | 1.73 |
| 28 | IPA | 100 | 15.01 | 2.55 | 3.26 |
| 29 | PGME | 100 | 14.96 | 2.03 | 6.24 |
| 30 | IPA | 100 | 15.01 | 1.65 | 4.03 |
| 31 | PGME | 50 | 15.17 | 4.71 | 4.35 |
| 32 | IPA | 50 | 15.51 | 2.08 | 2.69 |

Figure 4:
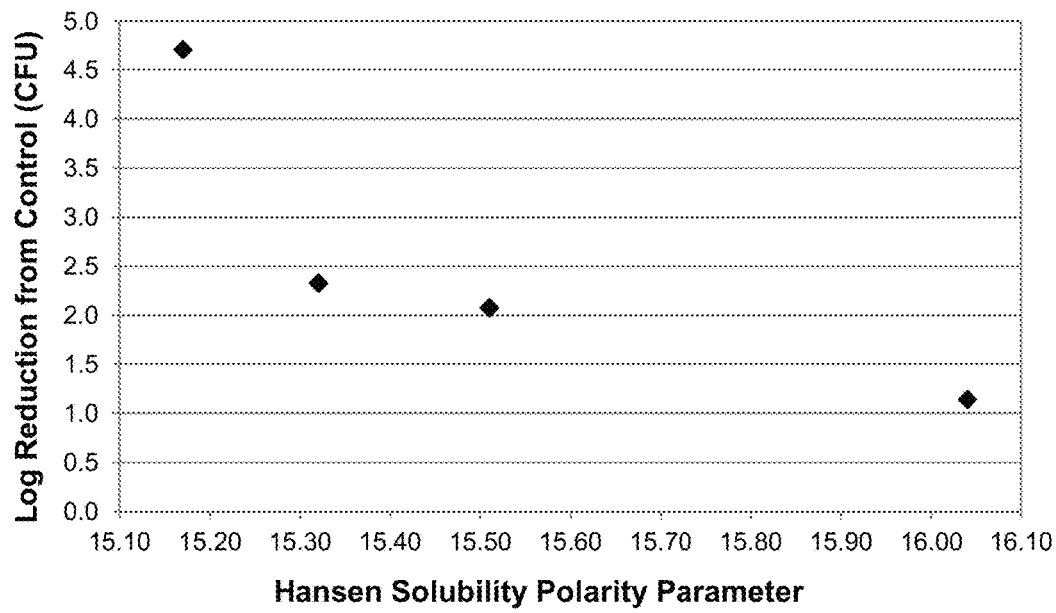
FIG. 4 depicts CDC reactor (biofilm) testing results for compositions employing cationic surfactant at pH=10 and 2.33 Osm/L, with S. aureus bacterial reductions plotted against $\delta_p$ values of the solvent component of antimicrobial compositions.
Figure 5:
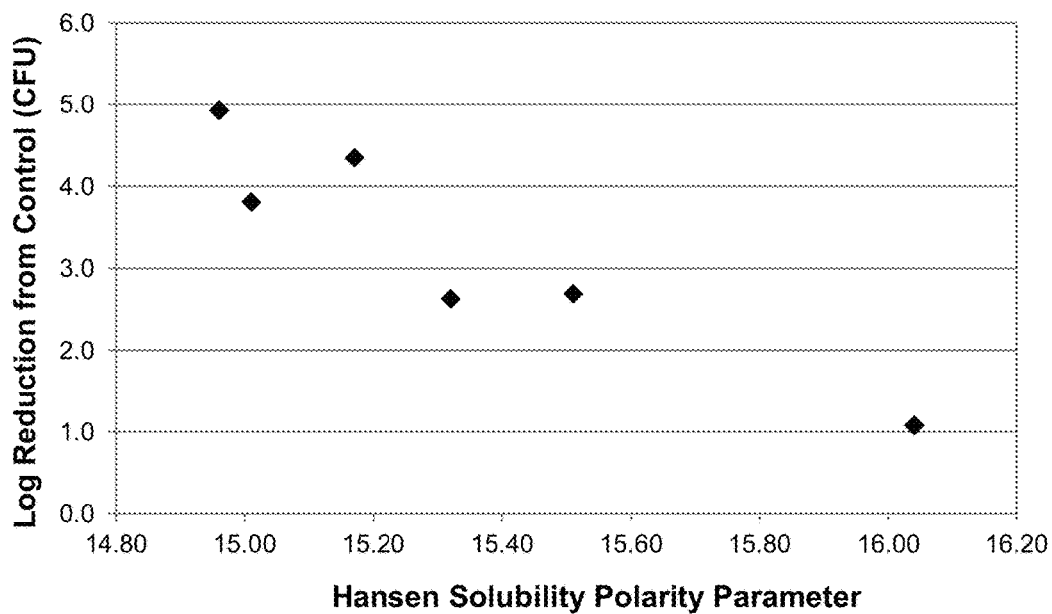
FIG. 5 depicts CDC reactor (biofilm) testing results for compositions employing cationic surfactant at pH=10 and 2.33 Osm/L, with P. aeruginosa bacterial reductions plotted against $\delta_p$ values of the solvent component of antimicrobial compositions.

The pH=10 and 2.33 Osm/L compositions from Examples 1-24 and 25-32 were identified, and their log reduction vs. $\delta_p$ value data were plotted, with the results being shown in FIGS. 4 (S. aureus) and 5 (P. aeruginosa), which show significant enhancement in antimicrobial activity near $\delta_p$ value 15.3 MPa$^{1/2}$.

Examples 33-43

To eliminate test-to-test variation and remove potentially confounding effects of using different solvents, the biofilm testing employed in Examples 1-24 was performed on compositions having varying concentrations of one solvent (PGME) at concentrations of from 0 to 10% w/v and varying amounts of exposure time.

The PGME was added to a composition containing 2.1 g/L BK, 19.4 g/L NaOH, and 65.0 g/L KH$_2$PO$_4$ (pH=10.0 and 2.33 Osm/L).

Figure 6:
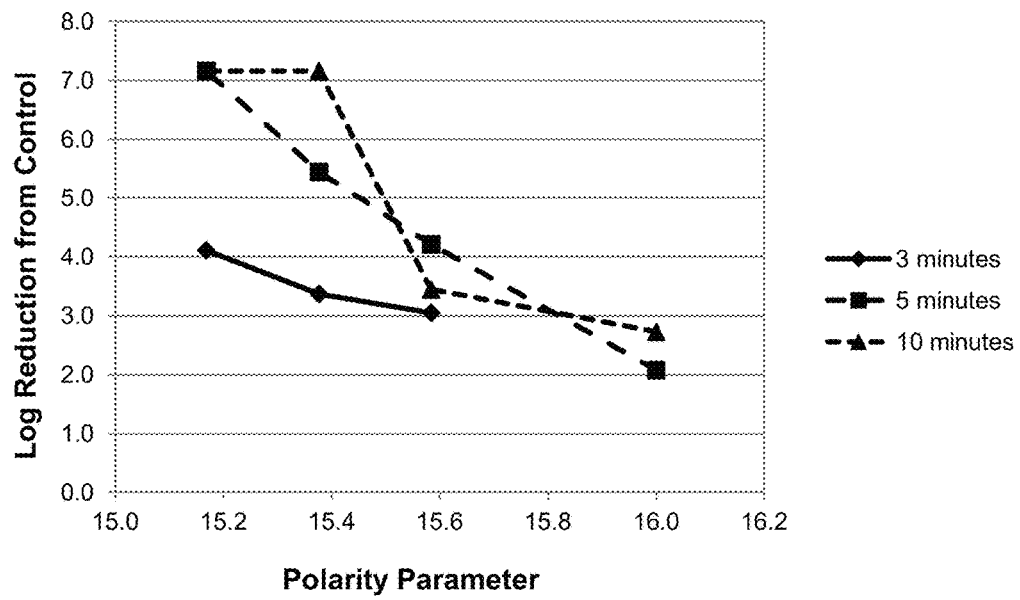
FIG. 6 depicts CDC reactor (biofilm) testing results (3-, 5- and 10-minute residence times) for compositions employing cationic surfactant at pH=10 and 2.33 Osm/L, with P. aeruginosa bacterial reductions plotted against $\delta_p$ values of the solvent component of antimicrobial compositions.

Bacterial reduction data from these tests plotted against $\delta_p$ values are shown in FIG. 6, which indicates that composition efficacy increases dramatically as the $\delta_p$ value of the solvent component decreases and with increasing application time. (The 10 minute applications at $\delta_p$=15.38 and $\delta_p$=15.17 MPa$^{1/2}$ and the 5-minute application at $\delta_p$=15.17 MPa$^{1/2}$ yield complete disinfection of the biofilm. The composition that did not contain any added PGME was not tested at a 3-minute application time.)

Examples 44-64

To evaluate the efficacy of antimicrobial compositions in a medical application, testing was undertaken using a mixed-species biofilm wound model using a drip flow reactor. Mixed species biofilms usually are more difficult to disinfect and produce a wider variance of data.

A mixed species biofilm of P. aeruginosa and S. aureus was grown on hydroxyapatite coated microscope slides in a drip flow reactor at a low flow rate (10 mL/hour) to yield a biofilm of ~10$^7$ to 10$^8$ CFU/cm.

Test compositions then were applied to all but one of the slides for 5 minutes with no flow. After the slides were harvested, log reduction values were obtained by determining the amount of bacteria on the control slide and the test samples and subtracting the latter from the former.

The compositions tested were prepared similarly to those set forth above in Examples 1-24. The particular amounts of the various components were as follows:

examples 44-49—2.1 g/L BK, 21.7 g/L NaOH, 74.7 g/L KH$_2$PO$_4$ (pH=9.0 and 2.33 Osm/L), examples 50-52—2.1 g/L BK, 22.0 g/L NaOH, 73.7 g/L KH$_2$PO$_4$ (pH=10.0 and 2.33 Osm/L), examples 53-54—1.3 g/L BK, 48.0 g/L citric acid, 42.5 g/L sodium citrate dihydrate (pH=4.0 and 880 mOsm/L), examples 55-56—1.3 g/L BK, 0.5 g/L Na$_2$CO$_3$, 37.5 g/L NaHCO$_3$ (pH=8.0 and 880 mOsm/L), examples 57-59—1.3 g/L BK, 1.0 g/L Na$_2$CO$_3$, 75.0 g/L NaHCO$_3$ (pH=8.0 and 1.76 Osm/L), examples 60-62—1.3 g/L BK, 8.2 g/L NaOH, 28.2 g/L KH$_2$PO$_4$ (pH=9.0 and 880 mOsm/L), and examples 63-64—1.3 g/L BK, 16.4 g/L NaOH, 56.4 g/L KH$_2$PO$_4$ (pH=9.0 and 1.76 Osm/L).

The performances of these compositions in CDC biofilm testing are shown below in Table 8.

TABLE 8

Antimicrobial composotions & biofilm test results

| | Solvent | | $\delta_p$ | Biofilm, log reduction | |
|---|---|---|---|---|---|
| | Identity | g/L | (MPa$^{1/2}$) | S. aureus | P. aeruginosa |
| 44 | — | 0 | 16.00 | 1.76 | 0.89 |
| 45 | PGME | 50 | 15.48 | 3.07 | 2.33 |
| 46 | PGME | 80 | 15.17 | 3.59 | 3.28 |
| 47 | PGME | 100 | 14.96 | 4.07 | 3.69 |
| 48 | DGME | 50 | 15.66 | 1.45 | 1.75 |
| 49 | DGME | 100 | 15.32 | 1.64 | 2.10 |
| 50 | PGME | 100 | 14.96 | 3.33 | 3.03 |
| 51 | DGME | 50 | 15.66 | 1.26 | 2.15 |
| 52 | DGME | 100 | 15.32 | 2.17 | 2.33 |
| 53 | DGME | 100 | 15.32 | 1.34 | 0.40 |
| 54 | IPA | 100 | 15.01 | 1.50 | 1.79 |
| 55 | DGME | 100 | 15.32 | 0.74 | 0.70 |
| 56 | IPA | 100 | 15.01 | 1.89 | 0.91 |
| 57 | — | 0 | 16.00 | 0.96 | 0.20 |
| 58 | DGME | 100 | 15.32 | 0.74 | 0.70 |
| 59 | IPA | 100 | 15.01 | 1.41 | 2.06 |
| 60 | IPA | 100 | 15.01 | 1.52 | 1.30 |
| 61 | IPA | 150 | 14.52 | 1.71 | 1.86 |
| 62 | DGME | 100 | 15.32 | 0.84 | 0.74 |
| 63 | — | 0 | 16.00 | 1.51 | 0.71 |
| 64 | IPA | 100 | 15.01 | 2.06 | 1.42 |

For all buffer system and pH values and for all bacteria, compositions with lower $\delta_p$ values exhibited increased efficacy relative to similar compositions having higher $\delta_p$ values, although some variation due to buffer system and particular bacteria was noted. Nevertheless, in general, a substantial increase in efficacy can be seen as the $\delta_p$ value decreases from ~15.5 to ~15.1 MPa$^{1/2}$.

Examples 65-80

Further testing was performed to provide additional insight into the relative importance of pH and osmolarity, as well as to consider the relative effects of other $\delta_p$ value-adjusting organic liquids.

The compositions tested were prepared similarly to those set forth above in Examples 1-24. The particular amounts of the various components were as follows:

examples 65-66—19.0 g/L NaOH, 66.0 g/L KH$_2$PO$_4$ (pH=7.5 and 2.33 Osm/L), examples 67-68—9.7 g/L NaOH, 32.5 g/L KH$_2$PO$_4$ (pH=10.0 and 1.165 Osm/L), examples 69-70—63.5 g/L citric acid, 56.3 g/L sodium citrate dihydrate (pH=4.0 and 1.165 Osm/L), examples 71-76, 79—19.4 g/L NaOH, 65.0 g/L $KH_2PO_4$ (pH=10.0 and 2.33 Osm/L), example 77—127.0 g/L citric acid, 112.5 g/L sodium citrate dihydrate (pH=4.0 and 2.33 Osm/L), and examples 78, 80—9.5 g/L NaOH, 33.0 g/L $KH_2PO_4$ (pH=7.5 and 1.165 Osm/L).

Each of examples 65-77 also included 2.1 g/L BK, while examples 78-80 had no added surfactant.

In these examples, one of the following solvents were added: PGME, IPA, ethyl acetate (EA, $\delta_p$=5.3) or chlorobenzene (CB, $\delta_p$=4.3). The particular solvent added, the amount added, and the effectiveness of the resulting composition against biofilms in CDC reactor testing, are summarized below in Table 9.

TABLE 9

Antimicrobial compositions & biofilm test results

| | Solvent | | $\delta_p$ | Biofilm, log reduction | |
|---|---|---|---|---|---|
| | Identity | g/L | (MPa$^{1/2}$) | S. aureus | P. aeruginosa |
| 65 | PGME | 100 | 14.96 | 2.23 | 4.65 |
| 66 | IPA | 100 | 15.01 | 2.54 | 3.81 |
| 67 | PGME | 100 | 14.96 | 3.07 | 1.73 |
| 68 | IPA | 100 | 15.01 | 2.55 | 3.26 |
| 69 | PGME | 100 | 14.96 | 2.03 | 6.24 |
| 70 | IPA | 100 | 15.01 | 1.65 | 4.03 |
| 71 | PGME | 50 | 15.48 | 4.71 | 4.35 |
| 72 | IPA | 50 | 15.51 | 2.08 | 2.69 |
| 73 | IPA | 150 | 14.52 | 2.21 | 6.45 |
| 74 | EA | 100 | 14.93 | 2.78 | 3.95 |
| 75 | CB | 100 | 14.83 | 2.45 | 6.84 |
| 76 | CB | 130 | 14.46 | 2.68 | 5.73 |
| 77 | CB | 100 | 14.83 | 3.42 | 6.84 |
| 78 | PGME | 100 | 14.96 | 1.21 | 4.57 |
| 79 | IPA | 150 | 14.52 | 2.82 | 5.54 |
| 80 | PGME | 50 | 15.48 | 0 | 2.37 |

Figure 7:
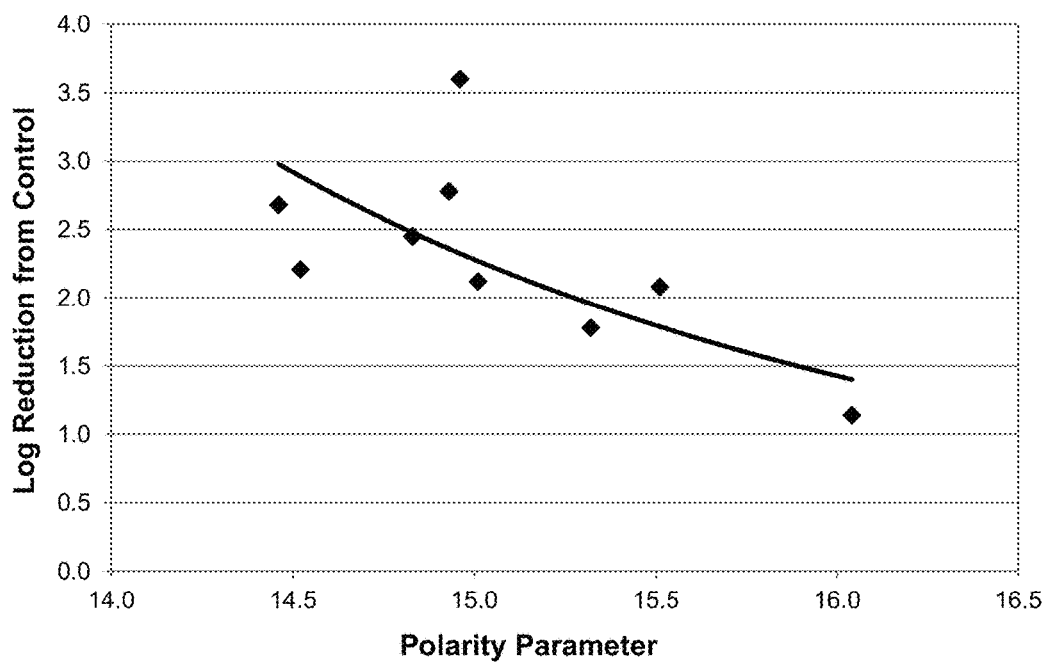
FIG. 7 depicts CDC reactor (biofilm) testing results for compositions at pH=10 employing cationic surfactant, with S. aureus bacterial reductions plotted against $\delta_p$ values of the solvent component of antimicrobial compositions.

Bacterial reduction versus $\delta_p$ value of the solvent component of the compositions from Examples 9-12 and 71-76 were plotted, with the results being shown as follows:

FIG. 7—S. aureus CDC reactor (biofilm), pH=10 composition, and

Figure 8:
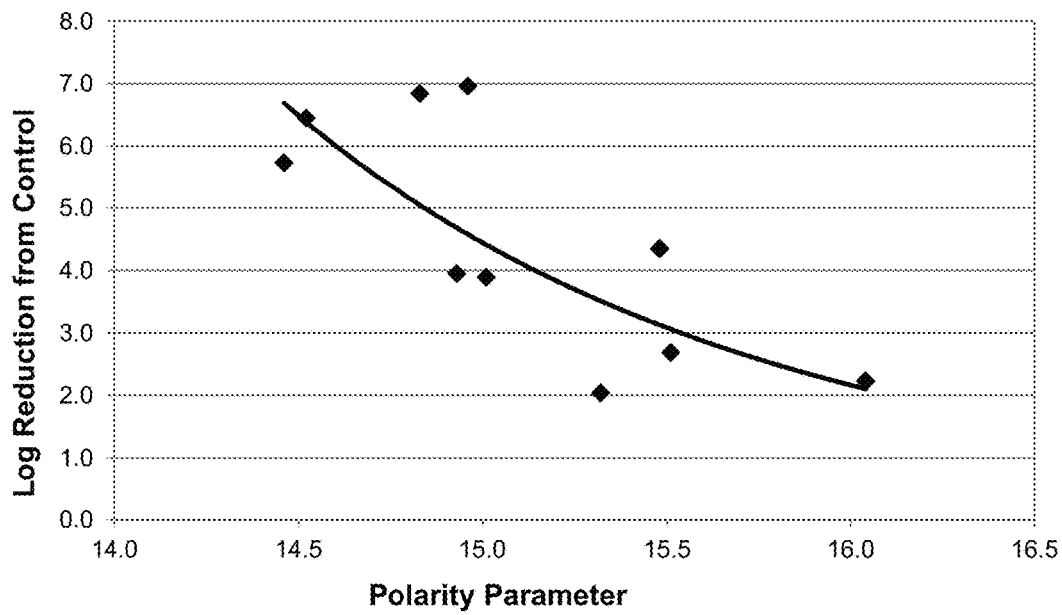
FIG. 8 depicts CDC reactor (biofilm) testing results for compositions at pH=10 employing cationic surfactant, with P. aeruginosa bacterial reductions plotted against $\delta_p$ values of the solvent component of antimicrobial compositions.

FIG. 8—P. aeruginosa CDC reactor (biofilm), pH=10 composition.

FIGS. 7-8 visually demonstrate that, as $\delta_p$ value decreases, efficacy against both S. aureus and P. aeruginosa increases, with the effect against the latter being more profound.

Figure 9:
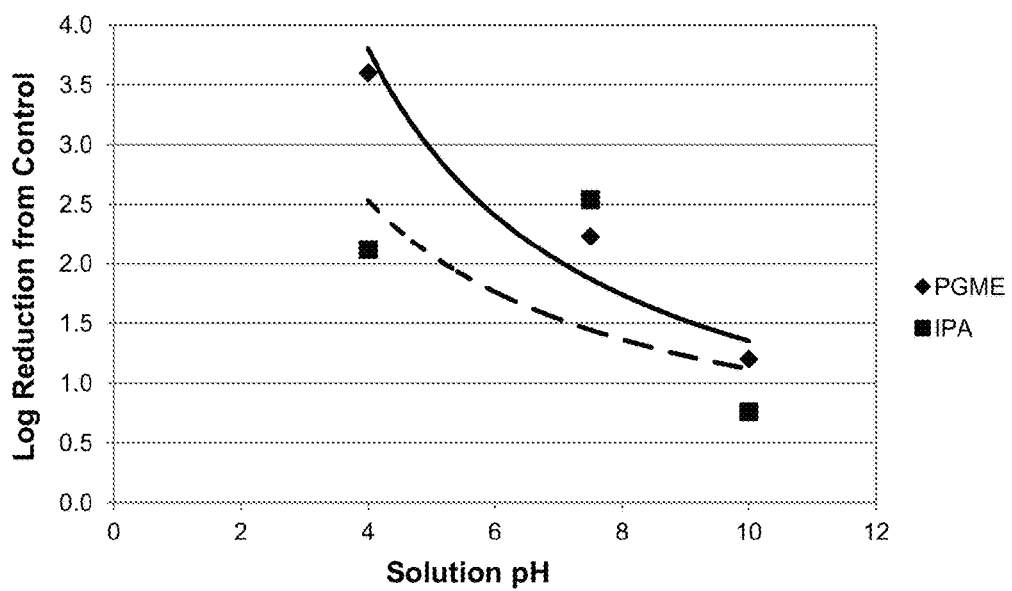
FIG. 9 depicts CDC reactor (biofilm) testing results for compositions having constant osmolarity, cationic surfactant concentration and solvent concentration, with S. aureus bacterial reductions plotted against pH values of the antimicrobial compositions.
Figure 10:
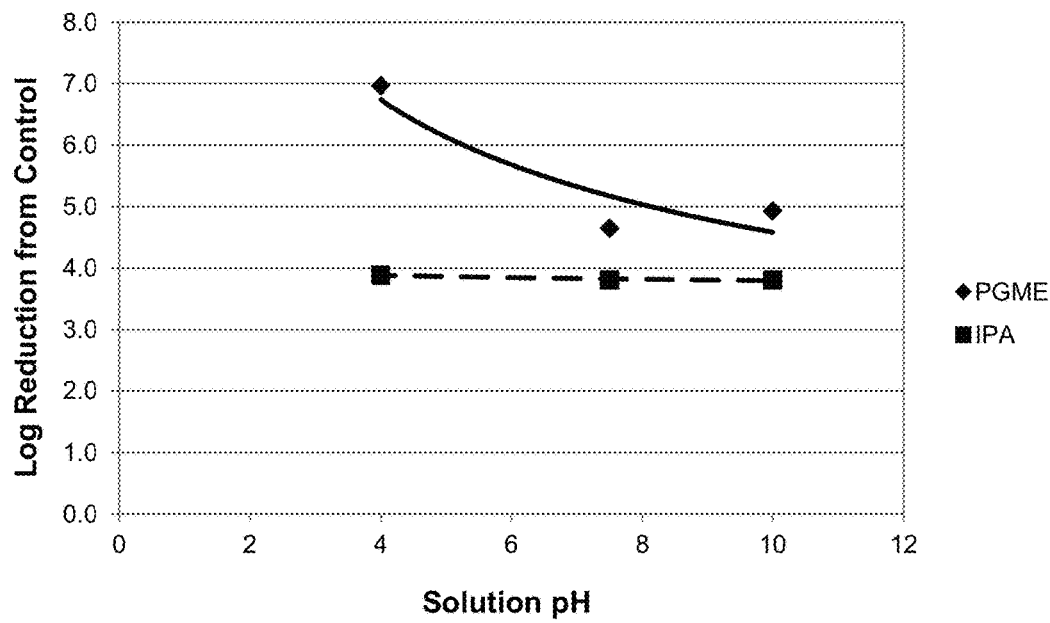
FIG. 10 depicts CDC reactor (biofilm) testing results for compositions having constant osmolarity, cationic surfactant concentration and solvent concentration, with P. aeruginosa bacterial reductions plotted against pH values of the antimicrobial compositions.

Bacterial reductions versus pH of the compositions of Examples 9 and 11, 13 and 15, and 65-66 (all of which had 10% (w/v) solvent, 2.1 g/L cationic surfactant, and 2.33 Osm/L) were plotted, with the results being shown in FIG. 9 (S. aureus) and FIG. 10 (P. aeruginosa). These plots seem to indicate that acidic compositions (lower pH values) have greater efficacy than higher pH solutions for S. aureus, while compositions with more neutral values are quite effective against P. aeruginosa. Based on this, composition osmolarity appears to impact efficacy more strongly than pH, a characteristic that suggests that moderate, surface-friendly compositions still can be very effective against target bacteria.

Figure 11:
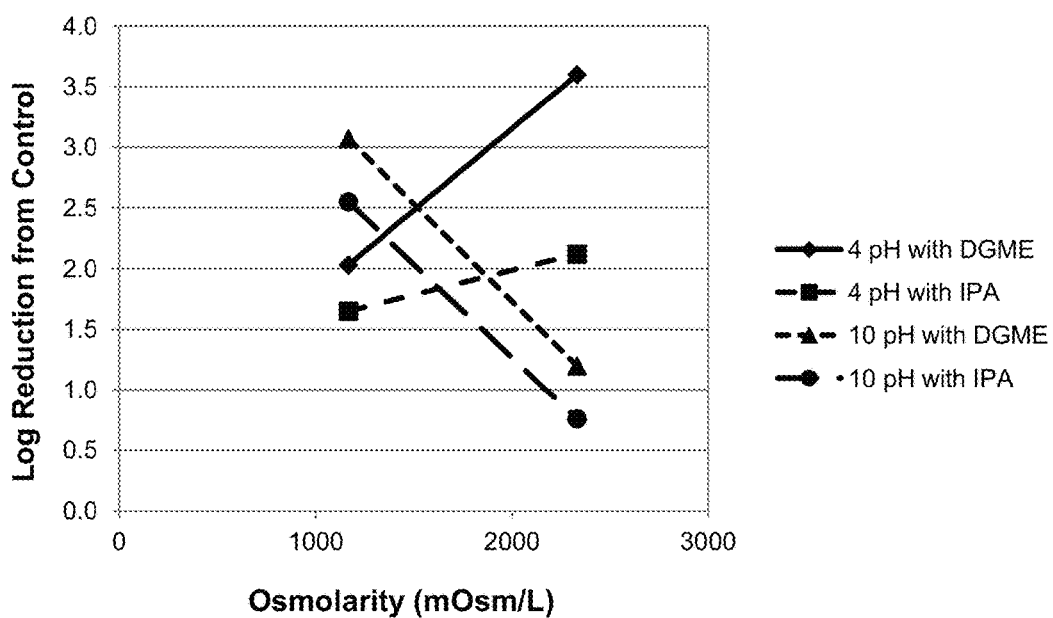
FIG. 11 depicts CDC reactor (biofilm) testing results for compositions having constant cationic surfactant concentration and solvent concentration, with S. aureus bacterial reductions plotted against osmolarity of the antimicrobial compositions.
Figure 12:
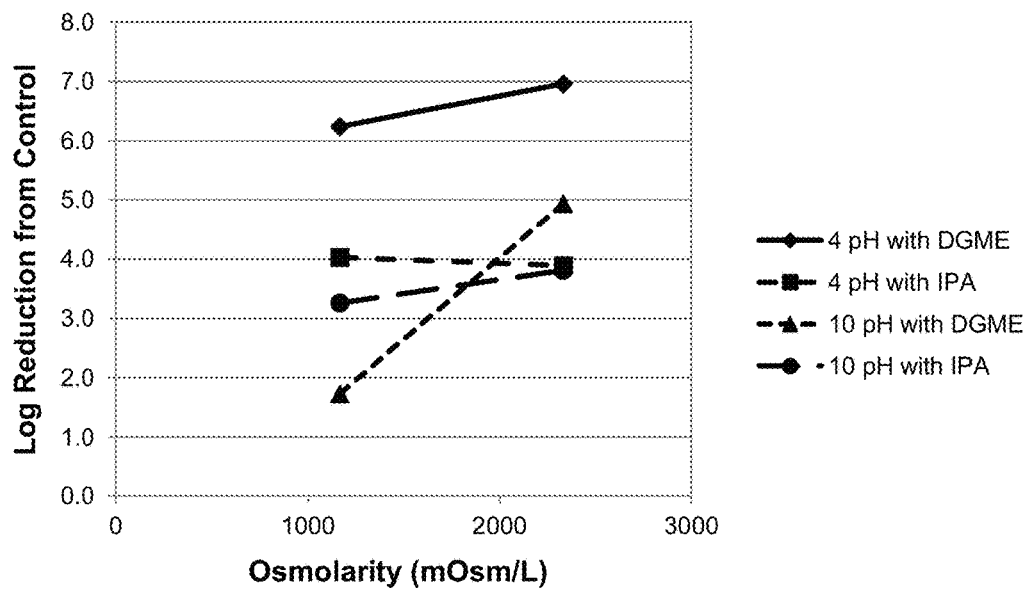
FIG. 12 depicts CDC reactor (biofilm) testing results for compositions having constant cationic surfactant concentration and solvent concentration, with P. aeruginosa bacterial reductions plotted against osmolarity of the antimicrobial compositions.

Bacterial reductions versus effective solute concentrations of the compositions from Examples 9, 11, 13, 15, 60, 67-68 and 70 (all of which contained 2.1 g/L cationic surfactant and 10% w/v organic liquid) were plotted, with the results being shown in FIG. 11 (S. aureus) and FIG. 12 (P. aerugi-nosa). In FIG. 11, the low pH compositions appear to present a trend toward increased efficacy with increasing effective solute concentration, but the high pH compositions do not seem to follow this trend. In FIG. 12, the DGME-containing compositions follow the expected trend of increased efficacy with increasing effective solute concentration, but the IPA-containing compositions do not.

Examples 81-88

Additional planktonic (AOAC) testing was performed to determine the effects of varying the $\delta_p$ value of the solvent component on the efficacy of compositions against soil-loaded S. aureus bacteria. Each composition employed $KH_2PO_4$ as buffer and IPA as solvent. The osmolarity of each composition was 2.33 Osm/L.

Thirty portions of each compositions were tested at 300 seconds each (soil-loaded bacteria samples at ~10$^6$ CFU/carrier.) Any visual indication of growth (i.e., color change from yellow to purple) was given a failing grade.

The percentage of passing tests are tabulated below, along with pH, amount of surfactant and $\delta_p$ value of the solvent component for each tested composition.

TABLE 10

Antimicrobial composition properties & planktonic testing results

| | pH | BK (%) | Solvent (%, w/v) | $\delta_p$ (MPa$^{1/2}$) | Pass (%) |
|---|---|---|---|---|---|
| 81 | 10 | 2.1 | 10 | 15.01 | 67 |
| 82 | 10 | 2.1 | 15 | 14.52 | 80 |
| 83 | 10 | 2.1 | 20 | 14.02 | 97 |
| 84 | 8.8 | 2.1 | 10 | 15.01 | 17 |
| 85 | 8.8 | 2.1 | 15 | 14.52 | 83 |
| 86 | 8.8 | 2.1 | 20 | 14.02 | 100 |
| 87 | 8.8 | 0.4 | 15 | 14.52 | 87 |
| 88 | 8.8 | 0.4 | 20 | 14.02 | 97 |

Figure 13:
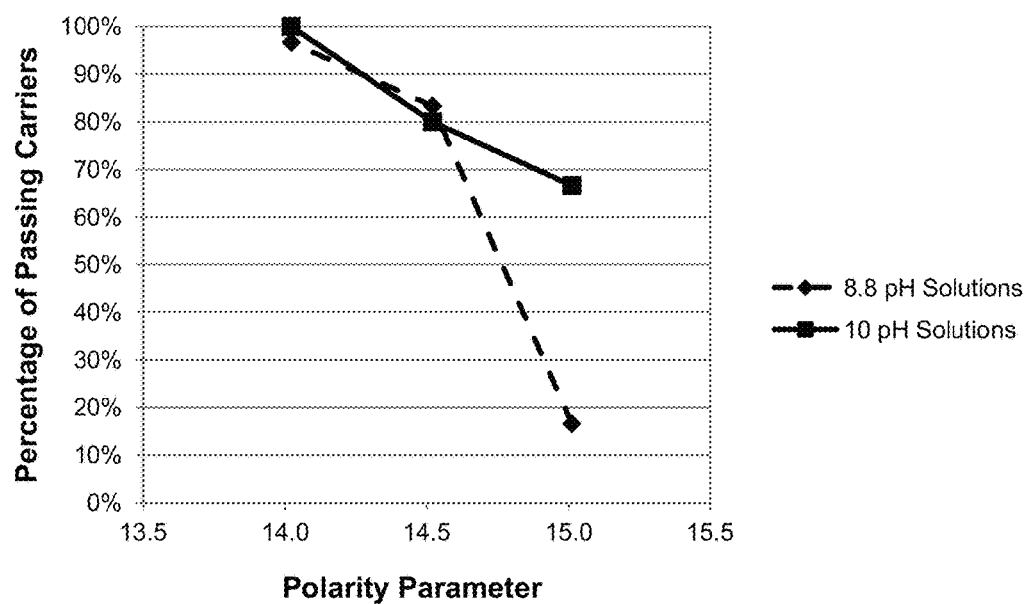
FIG. 13 depicts percent pass rates of antimicrobial compositions at constant osmolarity and surfactant concentration against soil-loaded S. aureus bacteria as a function of $\delta_p$ values at both pH=8.8 and pH=10.0 in 30 planktonic (AOAC) tests performed at 300 seconds each.

The data of Table 10 are plotted in FIGS. 13 (efficacy of the compositions as a function of the $\delta_p$ value of the solvent component) and 14 (efficacy of the compositions as a function of concentration of surfactant).

FIG. 13 clearly indicates a correlation between efficacy and decreasing $\delta_p$ value. The graph also seems to indicate that higher pH compositions retain efficacy even at higher $\delta_p$ values but that pH has little effect as the $\delta_p$ values pass a certain inflection point.

Figure 14:
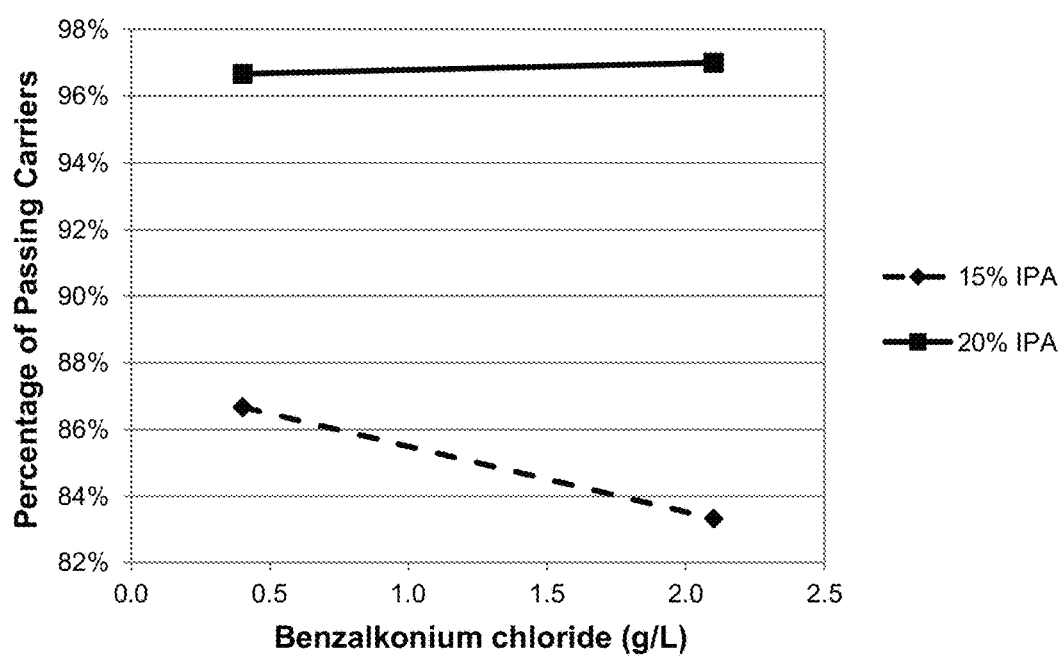
FIG. 14 depicts percent pass rates of antimicrobial compositions at constant osmolarity and pH against soil-loaded S. aureus bacteria as a function of cationic surfactant concentration at both 15% and 20% (w/v) solvent in 30 planktonic (AOAC) tests performed at 300 seconds each.

FIG. 14 indicates little effect due to change in surfactant concentration, although the effect of increasing the amount of IPA has a very large influence on efficacy, presumably due to the concomitant decrease in $\delta_p$ value of the solvent component.

That which is claimed is:

1. An antimicrobial composition adapted for dermal application, said composition comprising (a) a carrier base and (b) a liquid composition exhibiting an effective solute concentration of at least about 0.75 Osm/L and a pH of at least 3, wherein said liquid composition consists of
   (1) a solvent component that exhibits a $\delta_p$ value of no more than 14.4 MPa$^{1/2}$ and consists of water, one or more $C_1$-$C_{16}$ acyclic alcohols and, optionally, glycerol; and
   (2) a solute component that comprises cationic surfactant and dissociation products of at least two organic acids.

2. The antimicrobial composition of claim 1 wherein said liquid composition exhibits a pH of from 3.5 to 5.5.

3. The antimicrobial composition of claim 1 wherein said one or more $C_1$-$C_{16}$ acyclic alcohols comprises 2-propanol.

4. The antimicrobial composition of claim 1 wherein said at least two organic acids comprise one or more monoprotic acids.

5. The antimicrobial composition of claim 4 wherein said at least two organic acids further comprise one or more polyacids.

6. The antimicrobial composition of claim 5 wherein said solute component further comprises dissociation product of a salt of said one or more polyacids.

7. The antimicrobial composition of claim 4 wherein said one or more monoprotic acids comprises or is salicylic acid.

8. The antimicrobial composition of claim 7 wherein said at least two organic acids further comprise one or more polyacids.

9. The antimicrobial composition of claim 8 wherein said one or more polyacids comprises or is citric acid.

10. The antimicrobial composition of claim 9 wherein said solute component further comprises dissociation product of a salt of citric acid.

11. The antimicrobial composition of claim 8 wherein said solute component further comprises dissociation product of a salt of said one or more polyacids.

12. The antimicrobial composition of claim 1 wherein said cationic surfactant is benzalkonium chloride.

13. The antimicrobial composition of claim 12 wherein said benzalkonium chloride is present at up to 0.13 weight percent based on said liquid composition.

14. The antimicrobial composition of claim 1 comprising an oleaginous or absorption carrier base.

15. The antimicrobial composition of claim 1 comprising an emulsion carrier base.

16. A composition adapted for dermal application, said composition comprising:
   a) a carrier base and
   b) a liquid composition which exhibits an effective solute concentration of at least about 0.65 Osm/L and a pH of from 3.5 to 5.5, wherein said liquid composition consists of
     1) a solvent component that exhibits a $\delta_p$ value of no more than 14.4 $MPa^{1/2}$ and consists essentially of water, 2-propanol and, optionally, glycerol; and
     2) a solute component that comprises benzalkonium chloride, dissociation products of at least one monoprotic acid and at least one polyacid, and dissociation product of a salt of one of said at least one polyacid.

17. The composition of claim 16 wherein said at least one monoprotic acid comprises or is salicylic acid.

18. The composition of claim 17 wherein said at least one polyacid is citric acid.

19. The composition of claim 16 comprising an oleaginous or absorption carrier base.

20. The composition of claim 16 comprising an emulsion carrier base.

* * * * *